United States Patent [19]
Botstein et al.

[11] Patent Number: 5,139,936
[45] Date of Patent: * Aug. 18, 1992

[54] USE OF THE GAL1 YEAST PROMOTER

[75] Inventors: David Botstein, Brookline, Mass.; Ronald W. Davis, Menlo Park, Calif.; Gerald R. Fink, Brookline, Mass.; Alison Taunton-Rigby, Lincoln, Mass.; Robert G. Knowlton, Lexington, Mass.; Jen-i Mao, Bedford, Mass.; Donald T. Moir, Waltham, Mass.; Christopher G. Goff, Haverford, Pa.

[73] Assignee: Collaborative Research, Inc., Waltham, Mass.

[ * ] Notice: The portion of the term of this patent subsequent to Apr. 28, 2004 has been disclaimed.

[21] Appl. No.: 283,812

[22] Filed: Dec. 13, 1988

Related U.S. Application Data

[63] Continuation of Ser. No. 809,245, Dec. 16, 1985, abandoned, which is a continuation of Ser. No. 470,911, Feb. 28, 1983, Pat. No. 4,661,454.

[51] Int. Cl.$^5$ .................. C12P 21/02; C07H 15/12; C12N 15/12; C12N 15/20; C12N 15/18; C12N 9/64; C12N 1/18; C12N 15/79; C12N 1/16

[52] U.S. Cl. .................. 435/69.1; 536/27; 435/320.1; 435/256; 435/942; 435/69.5; 435/69.9; 435/226; 435/69.51; 435/69.4; 435/69.6; 435/172.3; 435/71.1; 935/6; 935/37; 935/60; 935/69

[58] Field of Search .................. 435/70, 172.3, 320.1, 435/68–69.1, 256, 942, 69.5, 69.9, 226, 69.51, 69.4; 935/6, 37, 60, 69, 71.1; 536/27

[56] References Cited

U.S. PATENT DOCUMENTS

| | | | |
|---|---|---|---|
| 4,443,539 | 4/1984 | Fraser et al. | 435/68 |
| 4,468,464 | 8/1984 | Cohen et al. | 435/317 |

OTHER PUBLICATIONS

St. John et al. 1981. J. Mol. Biol. 152, 317–334.
Botstein, et al. 1982. in: The Molecular Biology of the Yeast Saccharomyces. Metabolism and Gene Expression. (Strathern etal. eds.) Cold Spring Harbor Laboratory. Cold Spring Harbor, N.Y. pp. 607–636.
Tuite et al, EMBO Journal vol. 1 No. 5 pp. 603–608 (1982).
Hitzeman et al, Nature vol. 293 pp. 717 to 722 Oct. 29, 1981.

Primary Examiner—Robert A. Wax
Assistant Examiner—Christopher S. F. Low
Attorney, Agent, or Firm—Wolf, Greenfield & Sacks

[57] ABSTRACT

A DNA segment contains a GAL1 promoter of Saccharomyces cerevisae linked to a gene other than the galoctokinase gene, for directing the expression of the gene within a yeast cell.

A GAL1 promoter portion of Saccharomyces cerevisae is linked to a foreign DNA segment for use in expressing a desired protein. Yeast cells containing the GAL1 promoter linked to a foreign DNA segment are grown in a medium containing glucose, wherein the yeast cells metabolize the glucose and are permitted to express a polypeptide when galactose is present in the medium.

33 Claims, 6 Drawing Sheets

```
          10        20        30        40        50        60
GAATTCGACAGGTTATCAGCAACACAGTCATATCCATTCTCAATTAGCTCTACCACAGTG 70        80        90       100       110       120
TGTGAACCAATGTATCCAGCACCACCTGTAACCAAAACAATTTTAGAAGTACTTTCACTT 130       140       150       160       170       180
TGTAACTGAGCTGTCATTTATATTGAATTTTCAAAAATTCTTACTTTTTTTTGGATGGA 190       200       210       220       230       240
CGCAAAGAAGTTTAATAATCATATTACATGGCATTACAACCATATACATATCCATATACA 250       260       270       280       290       300
TATCCATATCTAATCTACTATATGTTGTGGTATGTAAAGAGCCCCATTATCTTAGCCTAA 310       320       330       340       350       360
AAAAACCTTCTCTTTGGAACTTTCAGTAATACGCTTAACTGCTCATTGCTATATTGAAGT 370       380       390       400       410       420
ACGGATTAGAAGCCGCCGAGCGGGTGACAGCCCTCCGAAGGAAGACTCTCCTCCGTGCGT 430       440       450       460       470       480
CCTCGTCTTCACCGGTCGCGTTCCTGAAACGCAGATGTGCCTCGCGCCGCACTGCTCCGA
```

FIGURE 8

```
         490       500       510       520       530       540
ACAATAAAGATTCTACAATACTAGCTTTTATGGTTATGAAGAGGAAAAATTGGCAGTAAC 550       560       570       580       590       600
CTGGCCCCACAAACCTTCAAATGAACGAATCAAATTAACAACCATAGGATGATAATGCGA 610       620       630       640       650       660
TTAGTTTTTTAGCCTTATTTCTGGGGTAATTAATCAGCGAAGCGATGATTTTTGATCTAT 670       680       690       700       710       720
TAACAGATATATAAATGCAAAAACTGCATAACCACTTTAACTAATACTTTCAACATTTTC 730       740       750       760       770       780
GGTTTGTATTACTTCTTATTCAAATGTAATAAAAGTATCAACAAAAAATTGTTAATATAC 790       800       810       820
CTCTATACTTTAACGTCAAGGAGAAAAAACCCCGGATCC
```

FIGURE 8 (CONT'D)

USE OF THE GAL1 YEAST PROMOTER

This application is a continuation of application Ser. No. 06/809,245, filed Dec. 16, 1985 now abandoned, which is a continuation of Ser. No. 470,911, filed Feb. 28, 1983, now U.S. Pat. No. 4,661,454 issued Apr. 28, 1987.

BACKGROUND OF THE INVENTION

Developments in recombinant DNA technology have enabled the cloning in bacteria of the natural coding sequence of a variety of genes. [See Seeburg, P H., Shine, J., Martial, J. A., Baxter, J. D. and Goodman, H. M., *Nature* 270, 486–494 (1977) and Shine, J., Seeburg, P. H., Martial, J. A , Baxter, J. D. and Goodman, H. M., *Nature* 270, 494–499 (1977); Keshet, E., Rosner, A., Bernstein, Y., Gorecki, M. and Aviv, H., *Nucleic Acids Res* 9, 19 (1981); Miller, W. L., Martial, J. A and Baxter, J. D., *J. Biol. Chem.* 255, 7521–7524 (1980)]. Recently, recombinant DNA techniques have been described in which a foreign protein is cloned and expressed in yeast. Evidence for foreign gene expression in yeast came from studies on the in vivo transcription of a rabbit globin gene introduced into *Saccharomyces cerevisiae* on a yeast plasmid vector. [See Beggs, J. D , van den Berg, J., van Obyen, A , and Weissmann, C., *Nature* 283, 835–840 (1980).]

In an attempt to maximize expression of foreign genes in yeast, their 5'-promoter region, translation start and signal peptide sequences were replaced with similar regions from the yeast genome. With bovine growth hormone, these regions were replaced with those from the yeast alcohol dehydrogenase (ADH1) gene. Full length, biologically active bovine growth hormone molecules were produced in yeast. [See Hitzeman, R. A., Hagie, F. E., Levine, H. L., Goeddel, D. V., Ammerer, G., and Hall, B. D., *Nature* 295, 717–722 (1981).] Other promoters were employed but demonstrated much less gene expression. The ability of having a single strong promoter is highly useful to permit the attainment of substantial levels of expression for a variety of genes in yeast.

It has now been discovered that promoters for the GAL1 galactokinase gene are such a promoters. In addition, these promoters are under glucose repression. Thus, it becomes practical to clone any one of a variety of genes including bovine growth hormone, interferon, pre-prorennin and prorennin in yeast with expression maximized by direction of a yeast GAL1 promoter.

SUMMARY OF THE INVENTION

It is an object of the present invention is to provide genetic recombinant material carrying a GAL1 promoter of the yeast galactokinase gene for use in expressing a desired protein.

Another object of the present invention is to provide a DNA segment containing a GAL1 promoter linked to a gene other than the galactokinase gene for directing the expression of the gene in a yeast cell.

It is a further object of the present invention to provide a method of expressing bovine growth hormone, interferon, prorennin, pre-prorennin or other polypeptides in a yeast cell by use of a GAL1 promoter linked to the corresponding bovine growth hormone gene, interferon gene, prorennin gene, pre-prorennin gene or other gene.

It is an additional object of the present invention to provide modified strains of *Saccharomyces cerevisiae* which produce desired polypeptide product under the control of a GAL1 promoter of the yeast galactokinase gene.

A further object of the present invention is to provide a method of producing products such as bovine growth hormone, interferon, prorennin, and pre-prorennin in yeast through recombinant DNA techniques employing a GAL1 promoter.

According to the present invention, the expression of a gene for a desired polypeptide product is controlled by a GAL1 promoter of a yeast strain such as *Saccharomyces cerevisiae*. The GAL1 promoter is a DNA segment that contains the transcription start signal for galactokinase in yeast. The sequencing information for the GAL1 promoter is shown in Table 1.

TABLE I
LISTING OF THE SEQUENCE GAL125 AND GAL126

```
         10         20         30         40         50         60         70         80
GAATTCGACAGGTTATCAGCAACACAGTCATATCCATTCTCAATTAGCTCTACCACAGTGTGTGAACCAATGTATCCAGC 90        100        110        120        130        140        150        160
ACCACCCTGTAACCAAAACAATTTAGAAGTACTTCACTTGTAACTGAGCTGTCATTTATATTGAATTTTCAAAAAATTC 170        180        190        200        210        220        230        240
TTACTTTTTTTTGGATGGACGCAAAGAAGTTAATAATCATATTACATGGCATTACCACCATATACATATCCATATACA 250        260        270        280        290        300        310        320
TATCCATATCTAATCTACTATATGTGTGGTATGTAAAGAGCCCCATTATCTTAGCTAAAAAAACCTTCTCTTTGGAAC 330        340        350        360        370        380        390        400
TTTCAGTAATACGCTTAACTGCTCATTGCTATATTGAAGTACGGATTAGAAGCCGCCGAGCGGGTGACAGCCCTCCGAAG 410        420        430        440        450        460        470        480
GAAGACTCCTCCCTGCGGTCCGTCGTCTTCACCGGTCGCCGTTCCTGAAACGCAGATGTGCCTCGCCGCCACTGCTCCGA 490        500        510        520        530        540        550        560
ACAATAAAGATTCTACAATACTAGCTTTATGGTTTATGGTTATGAAGGAAAAATTGGCAGTAACCTGGCCCCACAAACCTTCAA 570        580        590        600        610        620        630        640
ATGAACGAATCAAATTAACAACCATAGGATGATAATGCGATTAGTTTTTTTCTAGCCTTATTTCTGGGGTAATTAATCAGGCGA 650        660        670        680        690        700        710        720
AGCGATGATTTTGATCTATTAACAGATATATATAAATGCAAAAACTGCATAACCACTTAACTAATACTTTCAACATTTTC 730        740        750        760        770        780        790        800
GGTTTGTATTACTTCTTATTC ┌126  AAATGTAATAAAAGTATCAACAAAAAATTGTAATATACCTCTATACTTTAACGTCAAG
                      │    CTCTACCGGATCC
        810        820 └125 830        840        850        860        870        880
GAGAAAAACCCCGGATCC
```

A DNA segment is provided which contains a GAL1 promoter linked to a gene foreign to the yeast genome for directing the expression of the gene within a yeast cell. The segment is preferably a 0.755 or 0.82 kilobase DNA sequence from the yeast genome that contains signals for transcription of the GAL1 gene into mRNA and subsequent translation of the mRNA. The coding sequence for galactokinase is not present in this DNA fragment.

In a method for obtaining expression of a desired polypeptide product in yeast, a yeast GAL1 promoter is inserted in vitro in front of the gene for that polypeptide product which is contained in a chromosome or plasmid. These vectors are used to transform cells and this new genetic information is maintained in the cell and passed on to its progeny.

Synthesis of a polypeptide product using a GAL1 promoter is advantageous for several reasons:

GAL1 promoters are strong, leading to synthesis of significant amounts of polypeptide product.

the GAL1 promoter activity can be regulated by changing the yeast's carbon source permitting propagation of the yeast without the potentially deleterious effects of polypeptide production, since overly high levels of the product may be toxic to cells.

construction of a yeast strain with these properties is particularly desirable for commercial production of polypeptide products because of existing large-scale yeast fermentation technology and also because of the low toxicity of S. cerevisiae.

BRIEF DESCRIPTION OF THE DRAWINGS

FIG. 8 is an illustration of the GAL 1 sequence of Table 1.

DESCRIPTION OF THE PREFERRED EMBODIMENT

Microorganisms prepared by the genetic engineering processes described herein are exemplified by cultures now on deposit with the American Type Culture Collection, 12301 Parklawn Drive, Rockville, Md. These cultures were deposited by Collaborative Research, Inc. and are identified as follows:

Accession Number 20643, Strain Designation CGY196, deposited September, 1982;
Accession Number 20661, Strain Designation CGY457, deposited February, 1983;
Accession Number 20662, Strain Designation CGY461, deposited February, 1983;
Accession Number 20663, Strain Designation CGY528, deposited February, 1983.

Figure 1:
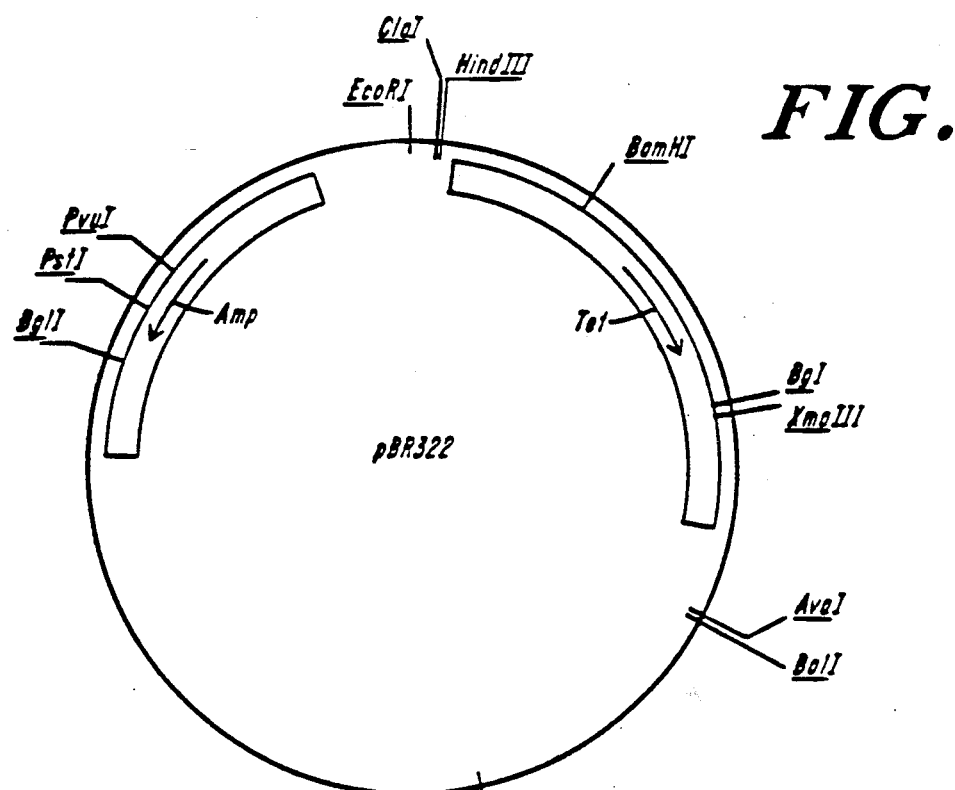
FIG. 1 is a diagrammatical showing of pBR322.

As more fully described below, a particular DNA segment is linked to a gene foreign to the yeast genome and incorporated in a modified strain of Saccharomyces cerevisiae so that it produces a polypeptide product under the control of a GAL1 promoter of the yeast galactokinase gene. The S. cerevisiae is genetically transformed with a novel recombinant DNA plasmid. The plasmid was constructed by ligation of DNA segments from the E. coli plasmid pBR322, yeast genomic and plasmid DNA's, and synthetic DNA linkers. The construction of plasmid pBR322, sequenced by J. G. Sutcliffe, Cold Spring Harbor Symposium 43, 77-90 (1979), is shown diagrammatically in FIG. 1.

Generally, in preparing the plasmid for joining with the exogenous gene, a wide variety of techniques can be used, including the formation of or introduction of cohesive termini. Blunt ends can be joined. Alternatively, the plasmid and gene may be cleaved in such a manner that the two chains are cleaved at different sites to leave extensions at each end which serve as cohesive termini. Cohesive termini may also be introduced by removing nucleic acids from the opposite ends of the two chains or alternatively, introducing nucleic acids at opposite ends of the two chains. Methods which may be employed in joining cleaved DNA segments depend on the nature of the termini, as described below.

"Blunt-ended" refers to DNA molecules with duplex base-paired termini. (See Sgaramella, V., van de Sande, J. H., and Khorana, H. G., Proc. Nat. Acad. Sci. USA 67, 1468-1475 (1970).) The DNA blunt-end termini may be joined by T4 DNA ligase with an apparent $K_m$ of about 50 μM DNA 5'-ends. (Sugino, A., Goodman, H. M., Heyneker, H. L., Shine, I., Boyer, H. W., and Cozzarelli, N. R., J. Biol. Chem. 252, 3987-3994 (1977).)

Blunt-ended DNA's are produced as for example, by cleavage with any of a number of restriction endonucleases, such as HaeIII. Alternatively, random shear breakage or a restriction enzyme making staggered cuts, such as EcoRI, HindIII, or BamHI, may be used, but the DNA termini must then be made blunt by biochemical methods. Such biochemical methods include incubation with single-strand-specific nuclease S1, as described in the following articles: Ulbrich, A., Shine, J., Chirgwin, J., Pictet, R., Tischer, E., Rutter, W. J., and Goodman, H. M., Science 196, 1313 (1977); Maniatis, T., Hardison, R. C., Lacy, E., Lauer, G., O'Connell, C., Guon, D., Sim, G. K., and Efstratiadis, A., Cell 15, 687 (1978); Scheller, R. H., Thomas, T. L., Lee, A. S., Klein, W H., Niles, W. D., Britten, R. J., and Davidson, H., Science 196, 197 (1977); and Charnay, P., Perricaudet, M., Galibert, F., and Tiollais, P, Nucleic Acids Res. 5, 4479 (1978). Alternatively, blunt termini can be created by incubation with T4 DNA polymerase [see Itakura, K., Hirose, T., Crea, R., Riggs, A. D., Heyneker, H. L., Bolivar, F., and Boyer, H. W., Science 198, 105: (1977); and Fraser, T. H., and Bruce, B. J., Proc. Nat. Acad. Sci. USA 75, 5936 (1978)], E. coli DNA polymerase [see Seeburg, P. H., Shine, J., Martial, J. A., Baxter, J. D., and Goodman, H. M., Nature 270, 486 (1977); Heffron, F., So, M., and McCarthy, B. J., Proc. Nat. Acad. Sci USA 75, 6012 (1978); and Backman, K., Ptashne, M. and Gilbert, W., Proc. Nat. Acad. Sci. USA 73, 4174 (1976)], and reverse transcriptase [see Ulbrich, A., Shine, J., Chirgwin, J., Pictet, R., Tischer, E., Rutter, W. J., and Goodman, H. M., Science 196, 1313 (1977)] with added deoxynucleotide triphosphates.

"Cohesive-ended" refers to DNA molecules with single-stranded termini. The single-stranded extensions are complementary and antiparallel. (See Mertz, J. E., and Davis, R. W., Proc. Nat. Acad. Sci. USA 69, 3370-3374 (1972).)

Joining of base-paired duplexes occurs when the nucleoside at a 5'-end carries a phosphate group and the complementary nucleoside opposite to it carries a free 3'-hydroxyl group. Two phosphodiester bonds would be made essentially simultaneously and the joined duplexes would have their nucleotide sequence inverted with respect to one another.

There are three general approaches to creating cohesive-ends on DNA:

1. digest DNA with type II restriction endonucleases that introduce staggered scissions at unique sequences;

2. treat linear DNA molecules with terminal deoxynucleotidyl transferase to generate single-stranded tails of either poly(dA) and poly(dT) or poly(dC) and poly(dG) at the 3'-hydroxyl terminus of different populations of DNA molecules; and 3. add to blunt-ended molecules linkers, which are short duplexes containing a restricton endonuclease cleavage site. Such linkers are joined to DNA by T4 DNA-ligase catalyzed blunt-end joining. After digesting the product with the restriction enzyme that cleaves the linker, the DNA is terminated with cohesive ends.

These methods are well known, as exemplified in the following articles: Sadler, J. R., Betz, J. L., Teiklenburg, M., Goeddel, D. V, Yansura, D. G., and Caruthers, M. H., *Gene* 3, 211 (1978); Bahl, C. P., Marians, K. J., Wu, R., Stawinsky, J., and Narang. S. A., *Gene* 1, 81 (1976); and Scheller, R. H., Dickerson, R. E., Boyer, H. W., Riggs, A. D., and Itakura, K., *Science* 196, 177 (1977).

"Linker" refers to a duplex, blunt-ended DNA molecule from 6-14 base pairs in length, containing the recognition site for a restriction endonuclease that produces cohesive termini.

In the preferred embodiment of the present invention, the plasmid serves as the vehicle for introduction of the foreign gene into the yeast cell. However, it is not necessary to use a plasmid, since any molecule capable of replication in yeast can be employed. The DNA molecule can be attached to a vector other than a plasmid, which can be a virus or cosmid as known in the art; or it can be integrated into the chromosome.

The recombinant plasmid or plasmid chimera is constructed in vitro. Since the annealing and ligation process not only results in the formation of the recombinant plasmid, but also in the recircularization of the plasmid vehicle, a mixture of ligation products is obtained involving the original plasmid and the foreign DNA. Only the original plasmid and the DNA chimera consisting of the plasmid vehicle and linked foreign DNA will normally be capable of replication. When the mixture is employed for transformation of the bacteria, replication of both the plasmid vehicle genotype and the foreign genotype will occur.

The transformation of the bacterial cells will result in a mixture of bacterial cells, the dominant proportion of which will not be transformed. Of the fraction of cells which are transformed, some significant proportion, but in some cases a minor proportion, will have been transformed by recombinant plasmid. In any event, only a very small fraction of the total number of cells which are present will have the desired phenotypic characteristics.

In order to isolate only the bacteria containing the DNA chimera or the original plasmid, a selectable genetic marker is included on the original plasmid, such as resistance to an antibiotic or heavy metal. The cells can then be grown on an agar medium containing the growth inhibiting substance. Since *E. coli* is used as the bacteria for transformation in the present invention, ampicillin is used as the growth inhibiting material to afford selection in *E. coli*. Only available cells having the resistant genotype will survive. If the foreign gene does not provide a phenotypical property, which allows for distinction between the cells transformed by the plasmid vehicle and the cells transformed by the plasmid chimera, a further step is necessary to isolate the replicated plasmid chimera from the replicated plasmid vehicle. The steps include lysing of the cells and isolation and separation of the DNA by conventional means or random selection of transformed bacteria and characterization of DNA from such transformants to determine which cells contain molecular chimeras. This is accomplished by physically characterizing the DNA by electrophoresis, gradient centrifugation, sequence analysis or electron microscopy.

Cells from various clones may be harvested and the plasmid DNA isolated from these transformants. The plasmid DNA may then be analyzed in a variety of ways. One way is to treat the plasmid with an appropriate restriction enzyme and analyze the resulting fragments for the presence of the foreign gene. Other techniques have been indicated above.

Once the recombinant plasmid has been replicated in *E. coli* and isolated, the *E. coli* may be grown and multiplied and the recombinant plasmid employed for transformation of the *S. cerevisiae* strain.

The term GAL1 promoter as employed in the present invention, also designated $P_{GAL1}$, is preferably either a 0.755 or 0.82' kilobase DNA sequence from the yeast genome which contains signals for transcription of the GAL1 gene into mRNA and subsequent translation of the mRNA. The coding sequence for galactokinase is not present in this DNA fragment, but the fragment can direct the expression of foreign genes and the regulation follows the mode for the GAL1 gene. [See St. John, T. P. and Davis, R. W., *J. Mol. Biol.* 152, 285.315 (1981).]

The bovine growth hormone gene referred to, which can be promoted by the promoter used in this invention, is a protein of about 22,000 daltons synthesized in anterior pituitaries. The hormone is required for pre-adult growth. Bovine growth hormone (BGH) contains a single polypeptide of 191 amino acids with two disulfide bridges synthesized initially as a pre-growth hormone containing an amino-terminal extension of 26 amino acid residues. [See Miller, W. L., Martial, J. A. and Baxter, J. D., *J. Biol. Chem.* 255, 7521–7524 (1980); Keshet, E., Rosner, A., Bernstein, Y., Gorecki, M. and Aviv, H., *Nucleic Acids Res.* 9, 19–30 (1980); and Lingappa, V. R., Deviller-Thiery, A. and Blobel, G., *Proc. Nat. Acad. Sci. USA* 74, 2432–2436 (1977).]

The interferon gene referred to, which can be promoted by the promoter used in this invention, is any one of the three classes of interferon genes described below:

(a) leukocyte—derived from leukocyte or lymphoblastoid cells, designated LeIFN or IFN-α;

(b) fibroblast—derived from fibroblast cells, designated FIFN or IFN-β; and (c) immune—derived from mitogen- or antigen-stimulated lymphoid cells, designated IFN-γ.

Such interferon genes are described in:

Goeddel, D. V., Leung, D. W., Drell, T. J., Gross, M., Lawn, R. M., McCandliss, R., Seeburg, P. H., Ullrich, A., Yelverton, E., and Gray, P. W., *Nature* 290, 20–26 (1981).

Allen, G. and Fantes, K. H., *Nature* 287, 408–411 (1980) and preceding reference.

Zoon, K. C., *Science* 207, 527–528 (1980).

Mantei, N., Schwartzstein, M., Streuli, M., Panam, S., Nagata, S., and Weissman, C., *Gene* 10, 1–10 (1980).

Streuli, M., Nagata, S., and Weissman, C., *Science* 209, 1343-1347 (1980).

Preferably in the methods of this invention pre-prorennin and prorennin can each be obtained by isolation of pre-prorennin DNA material. The pre-prorennin is a precursor of prorennin. By removing portions of the pre-prorennin DNA, one could obtain genetic material which will code for prorennin.

Pre-prorennin or prorennin genes in accordance with this invention comprise any nucleotide sequences coding for the amino acid sequence of pre-prorennin or prorennin respectively and exclude any intervening nucleotide sequences present in the genomic DNA encoding pre-prorennin or prorennin respectively. These genes are also provided attached to vectors which replicate in suitable host cells.

For the purpose of this application, the prorennin gene is defined as any sequence of nucleotides which codes for the prorennin molecule, the amino acid sequence of which is described in the literature (B. Foltmann, V. B. Pedersen, H. Jacobsen, D. Kauffman, and G. Wybrandt, *Proc. Nat. Acad. Sci. USA* 74, 2321-2324 [1977]).

The pre-prorennin gene includes the sequence of nucleotides coding for prorennin, but also includes 48 additional nucleotides on the 5' end which code for the amino-terminal precursor polypeptide found on the pre-prorennin enzyme.

The yeast strain employed as the host cell in the preferred embodiment of the present invention is *Saccharomyces cerevisiae*, a common laboratory strain of yeast used for its low toxicity and well-known genetic characteristics. This strain is readily cultivatable on a large scale. However, the recombinant DNA material of the present invention containing a GAL1 promoter can be used to express a polypeptide product in any yeast cells capable of transformation, including yeast mutants that alter regulation.

*Saccharomyces cerevisiae* is a yeast whose vegetative reproduction occurs by multilateral budding cells. Such cells are usually found in pairs or small clusters. The species is usually diploid where spores are produced directly in vegetative cells, but the species can also be grown in higher ploidy. In addition, S. cerevisiae forms an ascus with one to four spheroidal spores in each ascus. The ascus for this species does not rupture at maturity The yeast has a strongly fermentative as well as respiratory metabolism. Selected strains are referred to as distillers' yeasts and baker's yeast.

The vast majority of yeasts can be cultivated under relatively uniform conditions on common laboratory media. The usual growth requirements of yeast include:

(a) organic carbon compound for carbon and energy;

(b) organic or inorganic nitrogen for the synthesis of proteins and nucleic acids;

(c) various minerals (including compounds furnishing trace elements); and (d) frequently a mixture of vitamins.

Such growth requirements are met by yeast nitrogen base (YNB, obtained from Difco), a chemically defined medium which contains a number of trace elements, 9 vitamins, trace amounts of amino acids to stimulate growth of certain fastidious yeasts and the principal minerals, potassium phosphate, magnesium sulfate, sodium chloride, and calcium chloride. The nitrogen source is ammonium sulfate. The desired carbon source must be added and is normally at a concentration of 0.5-3%. Additions are made to this medium to fit particular strain requirements. The pH range of the medium is usually from pH 3-8. The preferred range is pH 4.5-6.5.

The starting point for obtaining the cells of the present invention is the use of recombinant DNA techniques known in the art to obtain the genetic material desired and to insert it into the host cell after which the host cell is cloned Preferably, the gene which one wishes to ultimately clone in yeast is isolated in a first step by obtaining messenger RNA of the gene from a primary source. In the case of BGH, this is obtained by isolation from the bovine pituitaries. The messenger RNA can be isolated as by the method of Deeley, et al. (R. G. Deeley, J. I. Gordon, A. T. H Burns, K. P. Mullinix, M. Bina-Stein, R. F. Goldberger *J. Biol. Chem.* 252 8310-8319 [1977]) and poly A-enriched RNA can be obtained by chromatography over oligo (dT) cellulose by the method of R. C. Desrosiers, K. H. Friderici, & F. M Rottman *Biochemistry* 14 4367-4374 (1975).

The messenger RNA is then converted to double-stranded DNA by conventional means. First, the complimentary copy of the DNA is made from the messenger RNA by conventional recombinant DNA means as by the use of AMV reverse transcriptase. For example, the methods of A. Efstratiadis, F. C. Kafatos, A. M. Maxam and T. Maniatis, *Cell* 7 279-288 (1976), R. Higuchi, G. V. Paddock, R. Wall and W. Salser, *Proc Nat. Acad Sci. USA* 73, 3146-3150 (1976), D. L. Kacian and J. C. Myers, *Proc. Nat. Acad Sci USA* 73, 2191-2195 (1976), M. P. Wickens, G. N. Buell and R. T. Schimke, *J. Biol. Chem.* 253, 2483-2495 (1978), G. M. Wahl, R. A. Padgett and G. R. Stack, *J. Biol. Chem.*, 254, 8679-8689 (1979) can be used to obtain the copy DNA (cDNA). The RNA portion can be disposed of by breaking the strands as known in the art using any of the above methods or by heat denaturing according to the method of Wickens, et al. (1978).

Next, enzymes such as *E. coli* DNA polymerase I or AMV reverse transcriptase can be used to turn the cDNA into double-stranded DNA using the methods of the publications above and J. I. Gordon, A. T. H. Burns, J. L. Christmann & R. G. Deeley, *J. Biol. Chem.* 253, 8629-8639 (1978).

Thirdly, synthetic linkers can be attached to both ends of the double-stranded DNA as for example by the use of HindIII or EcoRI synthetic oligonucleotide linkers using conventional methods such as described in R. H. Scheller, T. L. Thomas, A. S. Lee, W. H. Klein, W. D. Niles, R. J. Britten and E. H. Davidson, *Science* 196, 197-200 (1977), T. H. Fraser and B. J. Bruce, *Proc. Natl. Acad. Sci. USA* 75 5936-5940 (1978), A. Ullrich, J. Shine, J. Chirgwin, R. Pictet, E. Tischer, W. J. Rutter & H. M. Goodman, *Science* 196, 1313-1319 (1977), J. Shine, P. H. Seeburg, J. A. Martial, J. D. Baxter & H. M. Goodman, *Nature* 270, 494-499 (1977), or P. H. Seeburg, J. Shine, J. A. Martial, J. D. Baxter & H. M. Goodman, *Nature* 270, 486-494 (1977).

In a fourth step, the DNA molecule is integrated into the chromosome or attached to a vector which can be a plasmid, virus or cosmid as known in the art. Such vectors include:

pBR322 (F. Bolivar, R. L. Rodriguez, P. J. Greene, M. C. Betlach, H. L. Heyneker, H. W. Boyer, J. H. Crosa, S. Falkow, 1977 *Gene* 2 95-119)

pMB9 (R. L. Rodriguez, F. Bolivara, H. M. Goodman, H. W. Boyer, M. C. Betlach in "Molecular Mechanisms in the Control of Gene Expression" [D. P. Nierlich, W. J. Rutter, C. F. Fox, Eds.] 471 Academic Press New York 1976)

pSC101 (S. N. Cohen, A. C. Y. Chang, H. W. Boyer, R. B. Helling 1973 *Proc. Nat. Acad Sci. USA* 70 3240)

λgtWES (D. Tiemeier, L. Enquist, P. Leder *Nature* 263 526–527) (1976)

λcharon phages (F. R. Blattner, et al *Science* 196 161–169) (1977)

f1 R229 (J. D. Boeke *Molec. Gen. Genetics* 181, 288–291) (1981)

pJC75-58 (J. Collins *Methods in Enzymology* 68 309–326) (1979)

This step is again carried out outside of the final host cell. Useful techniques for this procedure are described in the references above in connection with the linkers as well as in the following publications: V. Hershfield, H. W. Boyer, C. Yanofsky, M. A. Lovett & P. R. Helinski, *Proc. Natl. Acad. Sci. USA* 71, 3455–3459 (1974), N. E. Murray & K. Murray, *Nature* 251, 476–482 (1974), F. R. Blattner et al, *Science* 196, 161–169 (1977).

In a fifth step, the recombinant DNA molecule can be introduced into the cytoplasm of the host cell line using conventional procedures such as described in M. Mandel & A. Higa (1970) *J. Mol. Biol.* 53 159–162, P. C. Wensink, D. J. Finnegan, J. E. Donelson & D. S. Hogness, *Cell* 3, 315–325 (1974), S. N. Cohen, A. C. Y. Chang and L. Hsu, *Proc. Natl. Acad. Sci. USA* 69, 2110–2114 (1972), H. M. Goodman, and R. J. MacDonald, *Methods in Enzymology* 68, 75–90 (1979), E. M. Lederberg and S. N. Cohen, *J. Bact.* 119, 1072–1074 (1974).

Recognition of the correct clone may be accomplished by the method of hybridization selection or by probing with synthetic oligonucleotides, (T. Taniguchi, Y. Fujii, Kuriyama and M. Muramatsu, *Proc. Natl. Acad. Sci. USA* 77, 4003–4006 (1980), R. P. Ricciardi, J. S. Miller & B. E. Roberts, *Proc. Natl. Acad. Sci. USA* 76, 4927–4931 (1979), D. L. Montgomery, B. D. Hall, S. Gillam and M. Smith, *Cell* 14, 673–680 [1978]).

The newly modified host cell is then cloned and expression of the material desired obtained. For example, the technique of Guarente, et al. using the lactose operon promoter, (1980) (L. Guarente, G. Lauer, T. M. Roberts & M. Ptashne, *Cell* 20, 543–553 1980], L. Guarente, T. M. Roberts & M. Ptashne, *Science* 209, 1428–1430 [1980]) allows one to obtain and optimize expression of foreign DNA.

Figure 3:
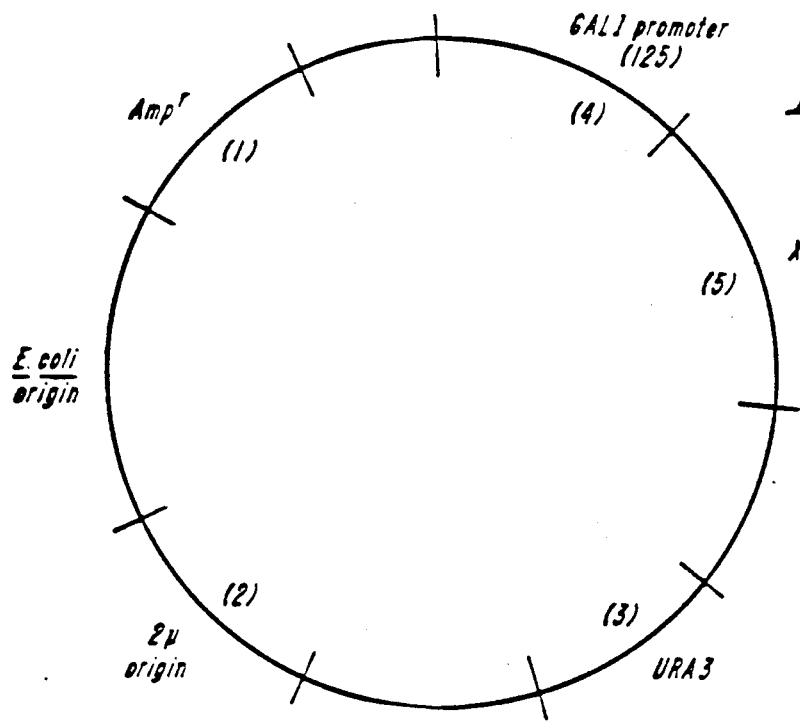
FIG. 3 is a diagrammatical showing of a representative plasmid construct.

In the present invention, the arrangement of the DNA segments in the plasmid construction is shown diagramatically in FIG. 3.

Figure 2:
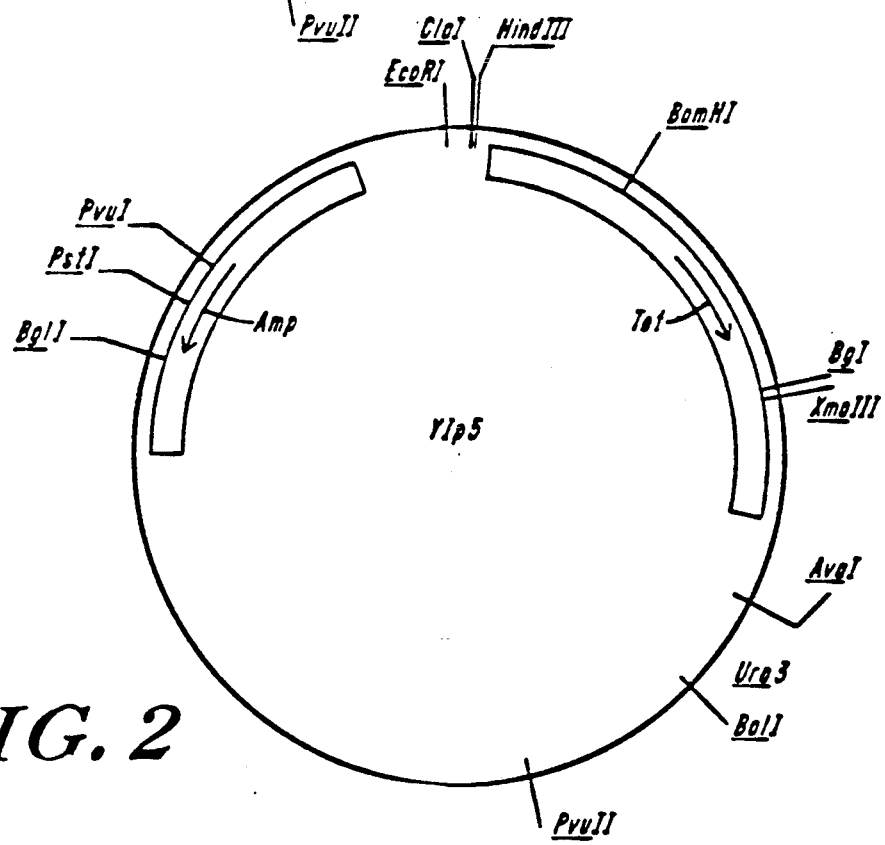
FIG. 2 is a diagrammatical showing of YIp5.

This construction consists of several components generally used in "shuttle" vectors, i.e., plasmids that can be maintained either in *E. coli* or yeast. The plasmid described in FIG. 3 is a modified construction of plasmid YIp5, as described by K. Struhl, D. T. Stinchcomb, S. Scherer and R. W. Davis, *Proc. Nat. Acad. Sci. USA* 76, 1035–1039 (1979) [see FIG. 2]. Segment (1) is a 2.4 kilobase fragment of plasmid pBR322 and contains a DNA replication origin and β-lactamase gene, allowing propagation of the DNA in *E. coli* and continuous selection for its presence by ampicillin resistance. Segment (2) is a 1.6 kilobase HpaI to HindIII fragment of the yeast 2μ plasmid containing an initiation site for replication in yeast. [The 2μ plasmid is described by J. L. Hartley and J. E. Donelson, *Nature* 286, 860–865 (1980)]. Segment (3) is the URA3 gene from the yeast genome (1.1 kb long) to allow the selection of yeast harboring the plasmid by virtue of its complementation of the ura3⁻ mutation in the host strain. [The URA3 gene is described by M. Bach, F. Lacroute and D. Botstein, *Proc Nat. Acad Sci. USA* 76,386–390 (1979).]

Segment (4) is a 0.755 or 0.82 kb fragment of DNA from the yeast genome which contains signals for transcription of the GAL1 gene into mRNA and subsequent translation of the mRNA. The GAL1 gene is repressed when the yeast strain is grown in high glucose medium. The coding sequence for galactokinase is not present in the 0.755 or 0.82 kb fragments. These pieces of DNA can direct the expression of foreign genes and the regulation follows the mode for the GAL1 gene as herein disclosed.

Segment (5) is a fragment of DNA which encodes for the desired polypeptide product sequence. This piece of DNA is oriented so that transcription of the mRNA is controlled by a GAL1 promoter. The sequence coding for the signal peptide was removed and an ATG translational initiation codon was incorporated. Therefore, a gene initiated by methionine is used for the studies.

The plasmid was constructed by ligation of DNA pieces from various sources and synthetic linkers. The sequence at the junction of the 0.82 kb GAL1 promoter and the foreign gene sequence is:

(I)

where X is the foreign gene. The sequence TCGACC is part of a synthetic SalI linker and CCCCGGATC is part of a BamHI linker.

The sequence at the junction of the 0.755 kb GAL1 promoter and the foreign gene sequence is:

where X is the foreign gene.

The plasmid was first cloned and amplified in *E. coli* and then transformed into yeast. Expression levels were determined for various genes using similar constructions. In the case of BGH, for example, a fusion gene of BGH' 'lacZ replaced the BGH gene (at X) in FIG. 3. This construction contains essentially the whole BGH sequence (only the coding sequence for 4 amino acids for the N-terminus is missing) and nearly the whole lacZ gene. By monitoring the β-galactosidase lacZ gene product) activity, approximately 80,000 molecules of fusion protein were produced per cell in strain CGY 150 (αleu2-3 ura3-52 GAL+).

Permissible modifications in the production of a polypeptide product in yeast would include:

Different terminators can be used.

With respect to BGH, the N-terminal amino acid is heterologous for BGH with both phenylalanine (Phe) and alanine (Ala) being observed. This heterogeneity is a consequence of ambiguous processing of the precursor molecule (pre-growth hormone). The gene described above codes for the Phe-BGH. The other gene for Ala-BGH can also be used for expression.

Mutations in the GAL1 promoter (element (4) in Table 4) can affect the level of expression or the mode of regulation. Other mutations in the chromosomal genome may also have the same effects. In fact, there are mutants available to turn a GAL1 promoter on constitutively. These strains can be used to get higher levels of expression.

The DNA segment containing P$_{GAL1}$ linked to the foreign gene (elements (4) and (5) in FIG. 3) can be integrated into the yeast chromosome for a stable construction rather than having this segment on an extrachromosomal plasmid.

The ATG initiation codon in the foreign gene can be replaced by other sequences such as sequences coding for a signal peptide. Further, the protein could be secreted from yeast cells into the medium.

Different lengths and sequences of DNA can be used at the junction of the GAL1 promoter and the foreign gene sequence to optimize the level of production. For instance, sequence (I) could be changed to:

P$_{GAL1}$-A$_6$ C C C C G C A A G C T T A T C G - A T G - X.     (II)

Other sequences in this region can be derived by performing mutagenesis.

Different length of the GAL1 promoter can be used. A terminator for transcription from the yeast genome can be added to the C-terminus of the BGH gene.

The term GAL1 promoter, as used herein, includes any portion of a 0.755 or 0.82 kilobase DNA sequence which acts to cause expression of galactokinase in yeast.

The yeast strain described herein will produce the desired polypeptide product if the medium contains galactose. The medium should contain 6.7 g/l yeast nitrogen base, 2% galactose and the appropriate amino acids. If the polypeptide product proves to be deleterious to the host strain, the production can be repressed by growing the yeast in a medium containing 2% glucose, 6.7 g/l yeast nitrogen base and then inducing the production of the polypeptide product after growth has ceased by transferring the yeast to the galactose medium. The cells are centrifuged and the cell-free extract is obtained by breaking cells by vigorous vortexing with glass beads.

EXAMPLE 1

Production of Bovine Growth Hormone

1. Isolation of BGH mRNA

Bovine pituitaries were collected shortly after killing and were frozen immediately on dry ice. 14.4 grams of tissue were disrupted by means of a Waring blender into 200 ml of cold buffer (10° C.) consisting of 50 mM Tris-HCl, pH 7.5, 8M guanidine HCl, and 1 mM dithiothreitol. The resulting solution was centrifuged at 5° C. in a Sorval SA600 rotor at 10,000 rpm for 17 minutes. The material was resuspended by homogenization and sat on ice for one hour in 40 ml of cold buffer consisting of 20 mM NaOAc, 20 mM EDTA, and then treated with half volume of ice-cold absolute ethanol. After 1 hour at −20° C., the precipitate was pelleted by a centrifugation at 3,000 rpm for 30 minutes at −10° C. The pellet was resuspended two times in 20 ml of the preceding buffer, treated with half volume of ice cold absolute ethanol, incubated one hour at −20° C. and the pellet collected as described previously. The final pellet was resuspended in 8 ml of 0.1M EDTA with heating at 60° C., and then 0.1 volume of 2M NaOAC, pH 5.0, and 2 volumes of ice-cold absolute ethanol were added and the solution placed at −20° overnight. The RNA precipitate was collected by centrifugation at 8.000 rpm for 20 minutes at −20° C., and was dissolved in 5 ml water. The yield was 5 mg RNA. The RNA solution was diluted with 5 ml of 2× concentrated binding buffer (20 mM Tris-HCl, pH 7.5; 2 mM EDTA, pH 7.0; 0.4% SDS; and 0.24M NaCl). The RNA was applied to a 1.5 ml oligo-dT-cellulose column, the column was washed with 1× concentrated binding buffer and then the poly A-containing RNA (mRNA) was eluted by washing the column with binding buffer containing no NaCl. About 100 mg of poly A-containing RNA were obtained. A portion of the poly A-containing RNA was translated in vitro in a rabbit reticulocyte lysate system [Pelham, H. R. B. and Jackson, R. J., *Eur. J. Biochem.* 67 247–256 (1976)] to confirm the isolation of mRNA coding for BGH.

2. Preparation of double-stranded copy DNA (cDNA)

About 2.5 μg of cDNA was synthesized from 25 μg of the poly A-containing RNA by incubation for one hour at 42° C. in 50 mM Tris-HCl, pH 8.3; 100 mM KCl; 8 mM MgCl$_2$; 0.4 mM dithiothreitol; 5 mM each dATP, dGTP and dTTP; and 20 μg/ml oligo (-dT)$_{12-18}$, containing 100 units reverse transcriptase and 1.3 μCiα-$^{32}$P-dCTP (1.8 Ci/mmole). After heating the reaction mixture at 100° C. for 3.5 minutes, quick chilling on ice for approximately 3 minutes and removing the precipitated protein by centrifugation, to the supernatant was added HEPES-NaOH, pH 6.9, to 100 mM; MgCl$_2$ to 5 mM; dithiothreitol to 0.5 mM; and deoxynucleoside triphosphates to 0.125 mM. Incubation of this mixture with 300 units of *E. coli* DNA polymerase I for 2.5 hours at 15° C. produced 1.8 μg of double-stranded cDNA. The DNA was phenol extracted, separated from unincorporated triphosphates by chromatography on Sephadex G-100 (13.5 ml column, 0.7 cm×35 cm, eluted with 20 mM NaCl) and ethanol precipitated overnight at −20° C. by addition of 1/10 volume 2M NaOAc, pH 5, and 2.5 volumes cold ethanol. The double-stranded cDNA was then treated with 8,000 units of S1 nuclease at 37° C. for one hour in buffer (0.3M NaCl, 30 mM NaOAc, pH 4.6, 3 mM ZnSO$_4$). The reaction was terminated by addition of EDTA to 10 mM, and Tris-HCl, pH 8.3, to 200 mM, and the mixture applied to a Biogel A-150m column (0.75 cm×40 cm) equilibrated and eluted with 10 mM Tris-HCl, pH 7.5, 250 mM NaCl and 1 mM EDTA. The peak fractions (0.5 ml each) of large molecular weight DNA were pooled and ethanol precipitated by addition of 1/10 volume 2M NaOAC, pH 5, and 2.5 volumes cold absolute ethanol.

3. Addition of EcoRI Linkers

The S1-treated double-stranded cDNA (0.21 μg) was incubated in buffer (60 mM Tris-HCl, pH 7.5; 8 mM MgCl; 5 mM dithiothreitol, 1 mM ATP and 5 mM of each deoxynucleoside triphosphate) with 9 units of *E. coli* DNA polymerase I at 10° C. for 10 minutes and then placed on ice. This blunt-ended double stranded cDNA was next incubated in 65 mM Tris-HCl, pH 7.5; 6 mM Mg Cl$_2$; 5 mM dithiothreitol; 1 mM ATP, with 160 pmoles of $^{32}$P-labelled EcoRI synthetic linker (100x excess over cDNA ends) and 4 blunt-end units of T4 DNA ligase at 15° C. for 5 hours, cooled on ice, treated with EcoRI restriction endonuclease (New England Biolabs, 9 units) in 100 mM Tris-HCl, pH 7.5, 50 mM NaCl, 5.6 mM MgCl$_2$ at 37° C. for 4 hours 45 minutes and then phenol extracted. The reaction was fractionated on a Biogel A-150m column (0.7 cm×31.5 cm). Fractions (0.5 ml each) containing high molecular weight DNA were pooled and ethanol precipitated.

This double stranded cDNA with EcoRI cohesive termini was then ligated to f1 phage CGF4 double-stranded DNA which had been cut open with EcoRI restriction endonuclease and treated with calf intestinal alkaline phosphatase by the method of H. Goodman and R. J. MacDonald [Goodman, H. M. and MacDonald, R. J., *Methods in Enzymol.* 68, 75–91 (1979)] to remove the terminal phosphates. The ligation reaction contained 60 mM Tris-HCl, pH 7.5; 6 mM $MgCl_2$; 7 mM dithiothreitol; 0.12 µg double-stranded cDNA; 1.2 µg CGF4 DNA; 0.5 mM ATP and 450 cohesive end units of T4 DNA ligase. Ligation was for 19 hours at 15° C.

4. Transfection of *E. coli* DB4548 with recombinant CGF4 DNA

*E. coli* strain CGE6 (DB4548; hsdR$^-$, hsdM$^+$, sup E, sup F, B1$^-$, met$^-$) was grown in 150 ml tryptone broth at 37° C. with shaking and harvested at $OD_{700}=5$ by centrifugation at 7,000 rpm for 10 minutes at 4° C. The cells were resuspended in 70 ml ice cold 50 mM $CaCl_2$ and allowed to sit at 0° C. for 30 minutes The suspension was then centrifuged at 7,000 rpm for 10 minutes at 4° C. and resuspended in 3 ml ice cold 50 mM $CaCl_2$. After standing at 0° C. for 2 hours the cells were used for transfection. Either 1 µl or 2 µl of 1:40 dilution of ligation reaction in 50 mM Tris-HCl, pH 7.5, was added to each of 12 tubes containing 50 ml sterile 50 mM Tris-HCl, pH 7.5. One-tenth milliliter of the $CaCl_2$-treated cells was added to each tube and the mixtures set on ice for 30 minutes. After warming to 37° C. for 2 minutes, 0.2 ml of CGE5 (JM101: J. Messing (1979), F'traD36 proAB lacIZ∇M15 in a ∇(lac pro) SupE thi$^-$ background) overnight culture and 3 ml of 0.7% soft agar were added, and the mixture poured into tryptone agar plates. Incubation at 37° C. overnight produced over 3000 plaques.

5. Identification of a recombinant-CGF4 carrying the bovine growth hormone sequence The plaques were transferred to nitrocellulose and probed as described by Benton and Davis [Benton, W. D. and Davis, R. W., *Science* 196, 180–182 (1977] using a $^{32}$P-labelled BGH cDNA. The phages which hybridize intensely to the cDNA probe were picked from the plates and stored in TY medium at 4° C. Samples of the intact phage were amplified by growth overnight on CGE5 cells, harvested by centrifugation, and subjected to electrophoresis in a 0.6% agarose gel containing 0.37M Tris-glycine, pH 9.5, and stained with ethidium bromide after treatment in 0.2 N NaOH for one hour and neutralization in 0.5M Tris-HCl, pH 7.4. The migration is inversely proportional to the log of the size of the phage DNA and allowed selection of about 45 phages carrying inserted BGH DNA of size of 600 to 1200 base pairs. Single stranded DNA was prepared by the method of Horiuchi, et al. [Horiuchi, K., Vovis, G. F. and Zinder, N. D., *J. Biol. Chem.* 249, 543–552 (1974)] and hybrid selection was carried out. The eluted RNA was translated in a reticulocyte lysate system by the method of Pelham and Jackson [Pelham, H. R. D. and Jackson, R. J., *Eur. J. Biochem* 67, 247–256] and analysis of the protein products revealed the production of authentic immunoprecipitable BGH. Double-stranded RFI DNA was prepared from the phages by the method of Moses, et al. [Moses, P. B., Boeke, J. D., Horiuchi, K. and Zinder, N. D., *Virology* 104, 267–273 (1980)]. Each DNA was rut with EcoRI and PstI restriction endonucleases and the resulting fragments analyzed on an agarose gel to confirm that the insert contained a PstI site. One of the phage DNA's which had a segment of about 350 base pair (bp) was chosen for further study. The DNA insert was sequenced by the method of Maxam and Gilbert [Maxam, A. M. and Gilbert, W., *Methods in Enzymol.* 68, 499–560 (1980)] as shown in Table 2.

TABLE 2

```
                    GAATTCCGGGTCCTGTGGACAGCTCACCAGCT
                         -100         -90
                                                                                  -82
                                                                                   |
                                                                                  -40
                                                                                   |
     ATG  CTG  CTC  TTC  GCC  CTG  CTG  GCC  CCC  CGG  ACC  TCC
     MET  LEU  LEU  PHE  ALA  LEU  LEU  ALA  PRO  ARG  THR  SER
     -29                                       -20

20
                                                                                   |
     GCT  ATG  TCC  TTG  GGC  CTG  CCC  TGG  ACT  CAG  GTG  GCA  GGC  GTG  TTC  CAT  CCA
     ALA  MET  SER  LEU  GLY  LEU  PRO  TRP  THR  GLN  VAL  ALA  GLY  VAL  PHE  HIS  PRO
                         -10                                                        1

80
                                                                                   |
     CTG  GCT  ACC  TTC  AAA  GAG  GCT  GTG  CGG  ATC  TAC  CTG  CAG  AGA  CAT  CAG
     LEU  ALA  THR  PHE  LYS  GLU  ALA  VAL  ARG  ILE  TYR  LEU  GLN  ARG  HIS  GLN
                    10                            20                              60 40

140
                                                                                   |
     CAG  GAC  AAT  ACC  CAG  TTT  GAG  CTC  TGC  TTC  ACC  ATC  CCG  TCA  GGA
     GLN  ASP  ASN  THR  GLN  PHE  GLU  LEU  CYS  PHE  THR  ILE  PRO  SER  GLY
                                   30                              50         120 60

200
                                                                                   |
     TCC  ATC  AAT  CAG  GGG  CCC  GTT  GCC  GAC  TTT  TGC  CTT  CGC  ATC  TCA  AAC  GCC
     SER  ILE  ASN  GLN  GLY  PRO  VAL  ALA  ASP  PHE  CYS  LEU  ARG  ILE  SER  ASN  ALA
                                                       70                   180 80

260
                                                                                   |
     AAG  GAG  AAT  CAG  CCC  AGC  AAA  CTC  TTC  GAG  ACC  ATC  TTC  AAC  CTG
     LYS  GLU  ASN  GLN  PRO  SER  LYS  LEU  PHE  GLU  THR  ILE  PHE  ASN  LEU
                                              90                   240 90

320
                                                                                   |
     CAG  TCG  TGG  CTT  GCC  CAG  CTG  AGC  AAG  GTC  TTC  AGC  TCA  AGC  CCG
     GLN  SER  TRP  LEU  ALA  GLN  LEU  SER  LYS  VAL  PHE  SER  SER  SER  PRO
                                                                   300 100

360
                                                                                   |
     GGC  ACC  GAC  CGT  GTC  TAT  GAG  AAG  CTG  AAG  GAC  AGA  CTG  GAG  GAA  GGC  ATC  GTG  GCC  CTG
     GLY  THR  ASP  ARG  VAL  TYR  GLU  LYS  LEU  LYS  ASP  ARG  LEU  GLU  GLU  GLY  ILE  VAL  ALA  LEU
                                       110                                        120
```

TABLE 2-continued

| | | | | | | | | 380 | | | | | | | 400 | | | | | 420 | | | |
|---|---|---|---|---|---|---|---|---|---|---|---|---|---|---|---|---|---|---|---|---|---|---|---|
| ATG | CGG | GAG | ACC | GAT | GGC | GAA | GTG | CCC | CGG | GCT | GGG | CAG | ATC | CTC | AAG | CAG | ACC | TAT | GAC |
| MET | ARG | GLU | THR | ASP | GLY | GLU | VAL | PRO | ARG | ALA | GLY | GLN | ILE | LEU | LYS | GLN | THR | TYR | ASP |
| | | | | | | | | | | | | | | | | 140 | | | |
| | | | | 440 | | | | | | | | 460 | | | | | 480 | | |
| AAA | TTT | GAC | ACA | AAC | ATG | CGC | AGT | GAC | GCG | CTG | CTC | AAG | AAC | TAC | GGT | CTG | CTC | TCC |
| LYS | PHE | ASP | THR | ASN | MET | ARG | SER | ASP | ALA | LEU | LEU | LYS | ASN | TYR | GLY | LEU | LEU | SER |
| | | | | | | 150 | | | | | | | | | 160 | | | |
| | | | 500 | | | | | | | | 520 | | | | | 540 | | |
| TGC | TTC | CGG | AAG | GAC | CTG | CAT | AAG | ACG | GAG | ACG | TAC | CTG | AGG | GTC | ATG | AAG | TGC | CGC | CGC |
| CYS | PHE | ARG | LYS | ASP | LEU | HIS | LYS | THR | GLU | THR | TYR | LEU | ARG | VAL | MET | LYS | CYS | ARG | ARG |
| | | | | | | 170 | | | | | | | | | | 180 | | | |
| | | | 560 | | | | | | | | 580 | | | | | 600 | | | |
| TTC | GCG | GAG | GCC | AGC | TGT | GCC | TTC | TAG | TTGCCAGCCATCTGTTGTTTGCCCCTCCCCGT |
| PHE | GLY | GLU | ALA | SER | CYS | ALA | PHE | |
| | | | | | | | 191 | |
| | | 620 | | | | | | 640 | | | | | 660 |
| GCCTTCCTTGACCCTGAAGGTGCCACTCCCACTGTCCTTTCCTAATAAAATGAGGAAAT |
| | | 680 | |
| TGCATCGCAAAAAAAAA |

6. Expression of BGH in *Saccharomyces cerevisiae*

Figure 4:
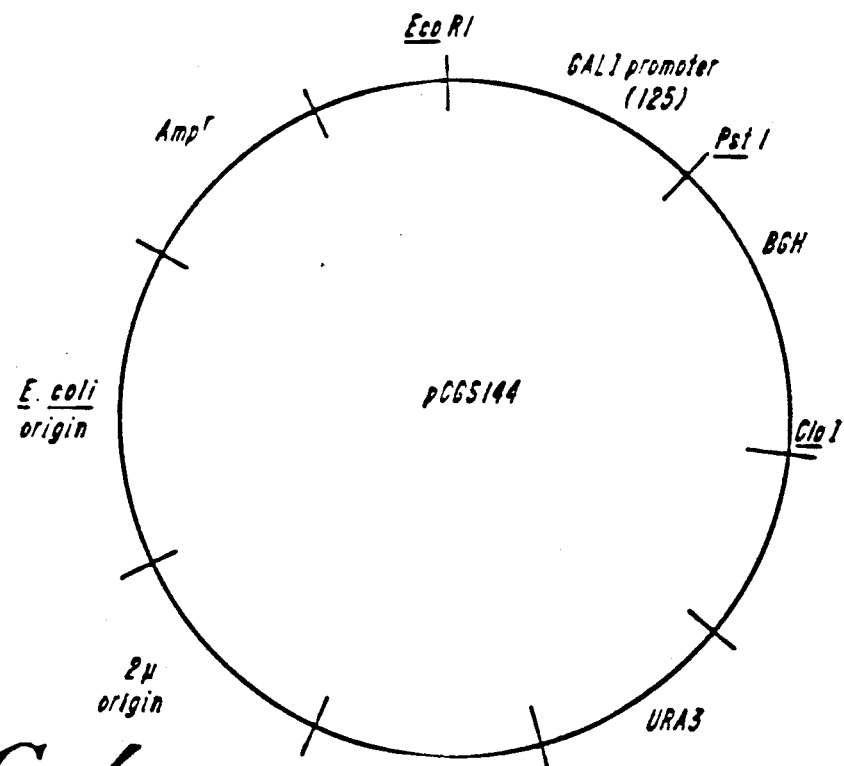
FIG. 4 is a diagrammatical showing of pCGS144.

A plasmid, pCGS144, as seen in FIG. 4, designed to facilitate obtaining expression of BGH in yeast was constructed. In order to produce the BGH in yeast, an ATG initiation codon was incorporated at the 5'-side of the first amino acid (phenylalanine). Based on the fact that HaeII cuts at the 3'-side of the first codon, a HaeII digest was carried out to open the 5'-end at the Phe codon. The cohesive ends were trimmed back by treating the DNA with 4 units *E. coli* DNA polymerase I (Klenow fragment) in the presence of 0.5 mM dATP in 6.6 mM Tris-HCl, pH 7.5; 6.6 mM NaCl; 6.6 mM $MgCl_2$ and 66 mM dithiothreitol, for 30 minutes at room temperature, and then blunt-ended with S1 nuclease.

A ClaI synthetic linker (CATCGATG) containing the ATG initiation codon was ligated onto the blunt-ended fragment in 66 mM Tris-HCl, pH 7.5; 10 mM $MgCl_2$; 10 mM 2.mercaptoethanol; 1 mM ATP with 500 pmole $^{32}$P-ClaI linker; 4 pmoles DNA (20 μg) and 4 blunt-end units of T4 DNA ligase at 17° C. overnight. This ligation created an ATG initiation codon and restored the first codon TGT. ClaI polylinker was removed by treating the fragment with 20 units restriction endonuclease ClaI for 3 hours at 37° C. in a 20 μl reaction containing 10 mM Tris-HCl, pH 7.5; 10 mM $MgCl_2$; and 0.1 mg/ml bovine serum albumin. The resulting fragment was cloned into the ClaI site of plasmid pBR322. The plasmid (10 μg) was cut with the restriction endonuclease ClaI (New England Biolabs, 20 units) for 2 hours at 37° C. in a 20 μl reaction containing 10 mM Tris-HCl, pH 7.5; 10 mM $MgCl_2$ and 0.1 mg/ml bovine serum albumin. The preparation of restriction cut plasmid was phenol extracted, ethanol precipitated and treated with calf intestinal phosphatase by the method of H. Goodman and R. J. MacDonald [Goodman, H. M. and MacDonald, R. J., *Methods in Enzymology* 68, 75-91 (1979)] to remove the terminal phosphates. Approximately 0.5 pmole of the ClaI fragment and 0.3 pmole of the ClaI cut plasmid were ligated together at 15° C. for 3 hours in a 20 μl reaction containing 66 mM Tris-HCl, pH 7.5; 6 mM $MgCl_2$; 10 mM dithiothreitol; 1 mM ATP; and T4 DNA ligase (New England Biolabs, 300 units) creating plasmid pCGE27.

Transformation-competent *E. coli* strain CGE43 (LG90; $F^-\nabla/$(lac-pro)Xlll) was prepared as described previously for CGE6, and 5 μl of the ligated DNA was mixed with 200 μl of the cells for 30 minutes at 0° C., heat treated at 37° C. for 2 minutes, incubated at room temperature for 10 minutes, and diluted five-fold with fresh tryptone broth. After incubation for 30 minutes at 37° C. with shaking, cells were plated on tryptone plates containing ampicillin (20 μg/ml). Ampicillin-resistant colonies were picked, and the plasmid DNA was prepared and analyzed by restriction enzyme digestion. By these criteria several cells carried the desired plasmid, pCGE27. Plasmid pCGE27 DNA (10 μg) was cut with the restriction endonuclease HindIII (Collaborative Research, Inc., 12 units) for 2 hours at 37° C. in a 20 μl reaction containing 10 mM Tris-HCl, pH 7.5; 10 mM $MgCl_2$; 60 mM NaCl; and 0.1 mg/ml bovine serum albumin). This DNA was next digested with the endonuclease EcoRI (Collaborative Research, Inc., 15 units) for 3 hours at 37° C. in a 20 μl reaction containing 100 mM Tris-HCl, pH 7.6; 10mM $MgCl_2$; 50 mM NaCl; and 1 mg/ml bovine serum albumin. The restriction cut DNA was trimmed back with *E. coli* DNA polymerase I (Klenow fragment) in the presence of 0.5 mM dTTP and made blunt-ended with S1 nuclease as described previously. The DNA was then phenol extracted, ethanol precipitated, redissolved in water and applied to a preparative horizontal 1.5% agarose gel. After electrophoresis for 2 to 3 hours in 40 mM Tris-acetate, pH 7.2, the gel was stained with ethidium bromide and examined under long wavelength ultraviolet light. The digested DNA was extracted by freezing and thawing the gel pieces [Thuring, et al., *Anal. Biochem.* 66, 213 (1975)]. The DNA fragment was ethanol-precipitated and redissolved in water. A plasmid (pGL101; 20 μg) containing 95 base pairs of $P_{lac}$ inserted at EcoRI/PvuII site of pBR322 was cut with the restriction endonuclease PvuII (New England Biolabs, 24 units) for 6 minutes at 37° C. The restriction cut DNA was phenol extracted, ethanol precipitated, and redissolved in water. This PvuII opened vector was analyzed by gel electrophoresis and excised from the gel (see above). Approximately 0.25 pmole of the DNA fragment coding for BGH was ligated into plasmid pGL101 opened at its PvuII site (see above) for 4 hours at 14° C. in a 20 μl reaction containing 66 mM Tris-HCl, pH 7.6; 6.6 mM $MgCl_2$; 10 mM dithiothreitol; 1 mM ATP and T4 DNA ligase (New England Biolabs, 300 units). Transformation-competent *E. coli* strain CGE43 cells were prepared exactly as described above, and 5 μl of the ligated DNA was mixed with 100 μl of the cells for 30 minutes at 0° C., heat treated at 37° C. for 2.5 minutes, and diluted ten-fold with fresh tryptone broth. After incubation for 30 minutes at 37° C. with shaking, cells were plated on tryptone plates containing ampicillin (20 μg/ml). Ampicillin-resistant colonies were picked, and the plasmid DNA was prepared and analyzed by restriction enzyme digestion for the correct orientation. By these criteria several strains carried the desired plasmid, pCGE22, which contained the $P_{LAC}$-Phe-BGH gene.

The fragment containing the gene for BGH was isolated from plasmid pCGE22 (30 μg) by partial cutting the plasmid with restricton endonuclease PvuII and PstI at 37° C. as above. The restriction cut DNA was phenol extracted, ethanol precipitated, redissolved in water and applied to a preparative 0.5% agarose gel. After electrophoresis in 40 mM Tris-acetate, pH 7.2, the gel was stained with ethidium bromide and examined under long wavelength ultraviolet light. The band was excised and the DNA extracted by freezing and thawing the gel pieces [Thuring, et al., *Anal. Biochem.* 66, 213 (1975)]. The DNA fragment was ethanol precipitated and redissolved in water. Approximately 0.5 pmole of the PvuII/PstI fragment was ligated into plasmid pCGE41 opened at its EcoRI site adjacent to the $P_{LAC}/'Z$ region and at PstI site. The EcoRI site was filled in with *E. coli* DNA polymerase I. Ligation was carried out for 2.5 hours at 14° C. in a 20 μl reaction containing 66 mM Tris-HCl, pH 7.6; 6.6 mM $MgCl_2$; 10 mM dithiothreitol; 1 mM ATP and T4 DNA ligase (Collaborative Research, Inc., 10 units). The ligated DNA was used to transform competent *E. coli* cells which were verified to contain the desired plasmid, pCGE51.

The plasmid, pCGE27, was cut with ClaI restriction enzyme, and the resulting fragment made blunt-ended with S1 nuclease. A SalI synthetic linker (GGTCGACC) was litaged onto the blunt-ended fragment. SalI polylinker was removed by treatment with 20 units restriction endonuclease SalI. It was then cut with PstI. The resulting fragment together with the PstI/XhoI BGH' 'Z fragment of pCGE51 were cloned into the yeast shuttle vector pCGS40 as described previously.

The plasmid, pCGS40, comprises most of pBR322 containing a DNA replication origin and β-lactamase gene for selection in E. coli, with a 1.6 kilobase fragment of the yeast 2μplasmid containing an initiation site for replication in yeast, with a 1.1 kilobase fragment from the yeast chromosomal DNA carrying a URA3 gene for selection in yeast and with a 0.9 kilobase fragment from yeast chromosomal DNA containing the SUC2 promoter of the yeast invertase gene. The plasmid pCGS40 was constructed by first cutting 60 μg of plasmid pRB118 [Carlson, M. and Botstein, D., Cell 28, 145-154 (1982)] with restriction endonuclease HindIII for 30 minutes at 37° C. and then with restriction endonuclease EcoRI (see above). The restriction cut DNA was phenol extracted, ethanol precipitated, redissolved in water and purified by gel electrophoresis. The digested EcoRI to HindIII 0.9 kilobase band which contains the promoter for the SUC2 gene was excised and the DNA extracted by glass beads. [Vogelstein, B. and Gillespie, D., PNAS 76, 615-619 (1979).] The 0.9 kilobase DNA fragment containing the SUC2 promoter was placed on the plasmid YIp5 (a shuttle vector which can be selected for and maintained in yeast due to the presence of the URA3 gene or E. coli due to the presence of the Amp gene). The resulting plasmid, pCGS46, obtained after ligation and transformation was purified and its structure verified. The plasmid pCGS40 was constructed by cutting the plasmid pCGS46 with restriction endonuclease PvuII for 1 hour at 37° C. A 1.56 kilobase fragment of 2μ DNA from plasmid YEp13, obtained from R. Davis, Stanford University, was removed by cutting YEp13 with HpaI and HindIII. The resulting fragment was gel purified, phenol extracted, ethanol precipitated, and treated with T4 DNA polymerase (see above) in order to create blunt ends at the HindIII restriction cut. After phenol extraction and ethanol precipitation, the PvuII cut DNA and blunt-ended 2μ DNA fragment were purified by gel electrophoresis and ligated together overnight. The resulting plasmid, pCGS40, can be grown and its presence can be selected for in either E. coli or Saccharomyces cerevisiae. Following transformation and restriction analyses, the desired plasmid, pCGS75, was obtained containing BGH' 'Z.

The plasmid, pCGS75, was cut with SalI and then rendered blunt-ended by treatment with E. coli DNA polymerase I. The blunt-ended DNA was then cut with XbaI and the fragment gel purified. This same plasmid was also cut with EcoRI/XbaI to produce a fragment which upon ligation with the previously isolated SalI-blunt-ended/XbaI fragment and an EcoRI/BamHI fragment of pBM125 yielded pCGS118 containing $P_{GAL1}$ BGH' 'Z on a yeast shuttle vector. The $P_{GAL1}$ promoter (820 bp) came from pBM125 (courtesy of R. Davis, Stanford University) which was cut with BamHI, filled in with E. coli DNA polymerase I then cut with EcoRI.

The construction of pCGS144 containing the BGH gene promoted b $P_{GAL1}$ was accomplished by a trimolecular reaction. The GAL1 promoter and part of the BGH gene were removed from pCGS118 by restriction with XbaI and PstI. The rest of BGH was obtained by cutting pCGE27 with PstI and ClaI. These gel purified fragments were ligated with a XbaI/ClaI fragment of pCGS57 which contained part of the 2μ and the URA3 gene.

The yeast strain CGY150 (MATa, leu 2-3, leu 2-112, ura 3-50) was transformed with the BGH plasmid DNA by the method of A. Hinnen, J. B. Hicks, and G. Fink [Hinnen, A., Hicks, J. B. and Fink, G. F., Proc. Nat. Acad. Sci. USA 75, 1929-1933 (1978)]. Yeast transformant CGY196, capable of growth without added uracil due to the presence of URA3 gene on the plasmid, were picked. (Strain CGY196 bearing plasmid pCGS144 is on deposit with the American Type Culture Collection (ATCC), Accession number 20643, deposited September, 1982.) The yeast cells were grown at 30° C. with agitation in a medium containing 6.7 g/l yeast nitrogen base, 30 mg/l L-leucine and 2% galactose. The synthesis of BGH was induced due to the presence of galactose. After growing to Klett=50 at 30° C. with agitation, the cells were collected by centrifugation, resuspended in 0.25 ml 0.05M Tris-HCl, pH 7.6, 20% glycerol and 1 mM PMSF, and frozen at −20° C. The cells were disrupted by glass beads by the method of M. Rose, et al. [Rose, M., Casadaban, M. J. and Botstein, D., Proc. Nat. Acad. Sci. USA 78, 2460-2464 (1981)] and the amount of BGH activity in the cellular extract was determined by immunoprecipitation.

The sequencing information for the bovine growth hormone gene produced is shown in Table 2.

EXAMPLE 2

Production of Interferon

1. Isolation of IFN mRNA 3.55 grams of Sendai virus induced lymphocytes were disrupted by means of a Dounce homogenizer into 40 ml of cold buffer (10° C.) consisting of 50 mM NaOAc, pH 5.2; 6M guanidine HCl; and 0.1M 2-mercaptoethanol The resulting solution was sonicated at 60W pulsed power for 2×30 seconds and then layered onto 3 ml shelves of 5.8M CsCl, pH 7.2, containing 0.1M EDTA. The material was centrifuged at 15° C. in a Beckman Type 50 Ti rotor at 40,000 rpm overnight. The pellet was resuspended on ice for 20 minutes in 6.6 ml of the above cold buffer plus 20 mM EDTA, and then treated with 3.3 ml of ice-cold absolute ethanol. After 1 hour at −20° C., the precipitate was pelleted by a centrifugation at 8,000 rpm for minutes at −10° C. The pellet was resuspended two times in 18 ml of the preceding buffer, treated with 9 ml of ice cold absolute ethanol, chilled one hour at −20° C. and the pellet collected as described previously. The final pellet was resuspended in 8 ml of 0.1M EDTA with heating at 60° C., and then 0.1 volume of 2M NaOAC, pH 5.0, and 2 volumes of ice-cold absolute ethanol were added and the solution placed at −20° overnight. The RNA precipitate was collected by centrifugation at 8,000 rpm for 20 minutes at −10° C., and was dissolved in 5 ml water. The yield was 396 mg RNA. The RNA solution was diluted with 5 ml of 2× concentrated binding buffer (20 mM Tris-HCL, pH 7.5; 2mM EDTA, pH 7.0; 0.4% SDS; and 0.24M NaCl). The RNA was applied to a 1 ml oligo-dT-cellulose column, the column was washed with 1× concentrated binding buffer and then the poly A-containing RNA (mRNA) was eluted by washing the column with binding buffer containing no NaCl. About 39 mg of poly A-containing RNA was obtained. A portion of the poly A-containing RNA was translated in vitro in a rabbit reticulocyte lysate system [Pelham, H. R. B. and Jackson, R. J., Eur. J. Biochem. 67, 247-256 (1976)] to confirm the isolation of mRNA coding for interferon.

2. Preparation of double-stranded copy DNA (cDNA)

About 2.5 μg of cDNA was synthesized from 25 μg of the lymphocyte poly A-containing RNA by incubation for one hour at 42° C. in 50 mM Tris-Hcl, pH 8.3; 100 mM KCl; 8mM MgCl$_2$; 0.4 mM dithioreitol; 1.2 mM each dATP, dGTP and dTTP; and 20 μg/ml oligo (-dT)$_{12-18}$, containing 100 units reverse transcriptase and 0.25 mM α-$^{32}$P-dCTP(1.8 Ci/mmole). After heating the reaction mixture at 100° C. for 3.5 minutes, quick chilling on ice for approximately 3 minutes and removing the precipitated protein by centrifugation, to the supernatant was added Hepes-NaOH, pH 6.9, to 100 mM; MgCl$_2$ to 5 mM; dithiothreitol to 0.5 mM; and deoxynucleoside triphosphates as above. Incubation of this mixture with 300 units of E. coli DNA polymerase I for 2.5 hours at 15° C. produced 1.8 μg of double-stranded cDNA. The DNA was phenol extracted, separated from unincorporated triphosphates by chromatography on Sephadex G-100 (13 ml column, 0.68 cm × 37 cm, eluted with 20 mM Tris-HCl, pH 7.5, 3.5 mM EDTA) and ethanol precipitated overnight at −20° C. by addition of 1/10 volume 2M NaOAc, pH 5, and 2.5 volumes cold ethanol. The double-stranded cDNA was then treated with 8,000 units of S1 nuclease at 37° C. for one hour in buffer (0.3M NaCl, 30 mM NaOAc, pH 4.6, 3 mM ZnSO$_4$). The reaction was terminated by addition of EDTA to 10 mM, and Tris-HCl, pH 8.3, to 200 mM, and the mixture applied to a Biogel A-150m column (0.7 cm × 35 cm) equilibrated and eluted with 10 mM Tris-HCl, pH 7.5, 250 mM NaCl and 1 mM EDTA. The peak fractions (0.5 ml each) of large molecular weight DNA were pooled and ethanol precipitated by addition of 1/10 volume 2M NaOAC, pH 5, and 2.5 volumes cold absolute ethanol.

3. Addition of HindIII Linkers

The S1-treated double-stranded cDNA (0.21 μg) was incubated in buffer (60 mM Tris-HCl, pH 7.5; 8 mM MgCl; 5 mM dithiothreitol, 1 mM ATP and 1 mM of each deoxynucleoside triphosphate) with 9 units of E. coli DNA polymerase I at 10° C. for 10 minutes and then placed on ice. This blunt-ended double stranded cDNA was next incubated in 65 mM Tris-HCl, pH 7.5;MgCl$_2$; 5 mM dithiothreitol; 1 mM ATP, with 160 pmoles of $^{32}$P-labelled HindIII synthetic linker (100×excess over cDNA ends) and 4 blunt-end units of T4 DNA ligase at 15° C. for 5 minutes, cooled on ice, heat treated to inactivate the ligase, treated with HindIII restriction endonuclease (New England Biolabs, 9 units) in 5.6 mM Tris-HCl, pH 7.5, 5.6 mM MgCl$_2$ at 37° C. for 4 hours 45 minutes and then phenol extracted. The reaction was fractionated on a Biogel A-150m column (0.7 cm × 31.5 cm). Fractions (0.5 ml each) containing high molecular weight DNA were pooled and ethanol precipitated.

This double stranded cDNA with HindIII cohesive termini was then ligated to f1 phage CGF4 double-stranded DNA which had been cut open with HindIII restriction endonuclease and treated with calf intestinal alkaline phosphatase by the method of H. Goodman and R. J. MacDonald [Goodman, H. M. and MacDonald, R. J., Methods in Enzymol. 68, 75-91 (1979)] to remove the terminal phosphates (Note: In order to produce phage CGF4, f1 phage R229 [Boeke, J. D., Mol. Gen. Genet. 181, 288-291 (1981)] was cut with EcoRI endonuclease, rendered blunt ended with T4 DNA polymerase and ligated with HindIII synthetic oligonucleotide linkers from Collaborative Research, Inc. of Lexington, Mass.) The ligation reaction contained 60 mM Tris-HCl, pH 7.5; 6 mM MgCl$_2$; 7 mM dithiothreitol; 0.12 μg double-stranded cDNA; 1.2 μg CGF4 DNA; 0.5 mM ATP and 450 cohesive end units of T4 DNA ligase. Ligation was for 19 hours at 15° C.

4. Transfection of E. coli DB4548 with recombinant CGF4 DNA

E. coli strain CGE6 (DB4548; hsdR$^-$, hsdM$^+$, sup E, sup F, Bl$^-$, met$^-$) was grown in 150 ml tryptone broth at 37° C. with shaking and harvested at OD$_{700}$=0.5 by centrifugation at 7,000 rpm for 10 minutes at 4° C. The cells were resuspended in 70 ml ice cold 50 mM CaCl$_2$ and allowed to sit at 0° C. for 30 minutes. The suspension was then centrifuged at 7,000 rpm for 10 minutes at 4° C. and resuspended in 3 ml ice cold 50 mM CaCl$_2$. After standing at 0° C. for 2 hours the cells were used for transfection. Either 1 μl or 2 μl of 1:40 dilution of ligation reaction in 50 mM Tris-HCl, pH 7.5, was added to each of 12 tubes containing 50 μl sterile 50 mM Tris-HCl, pH 7.5. One-tenth milliliter of the CaCl$_2$-treated cells was added to each tube and the mixtures set on ice for 30 minutes. After warming to 37° C. for 2 minutes, 0.2 ml of CGE5 (JM101: J. Messing (1979), F'traD36 proAB lacIZ∇M15 in a Δ(lac pro) SupE thi$^-$ background) overnight culture and 3 ml of 0.7% soft agar were added, and the mixture poured into tryptone agar plates. Incubation at 37° C. overnight produced over 1280 plaques.

5. Identification of a recombinant-CGF4 carrying the leukocyte interferon sequence The plaques were transferred to nitrocelluloses and probed as described by Benton and Davis [Benton, W. D. and Davis, R. W., Science 196, 180-182 (1977] using a $^{32}$P-labelled synthetic oligonucleotide (with the sequence, CATGATTTCTGCTCTGAC, Collaborative Research, Inc.) which corresponds to a known segment of LeIFN. The oligonucleotide (1 μg) was kinased with 0.5 mC γ-$^{32}$P-ATP using 6 units of T4 polynucleotide kinase (P-L Biochemicals) in a 20 μl reaction containing 66 mM Tris-HCl, pH 7.5, and 10 mM MgCl$_2$. The phage which hybridized intensely to the synthetic oligonucleotide probe were picked from the plates and stored in TY medium at 4° C. Samples of the intact phage were amplified by growth overnight on CGE5 cells, harvested by centrifugation, and subjected to electrophoresis in a 0.6% agarose gel containing 0.37M Tris-glycine, pH 9.5, and stained with ethidium bromide after treatment in 0.2N NaOH for one hour and neutralization in 0.5M Tris-HCl, pH 7.4. The migration is inversely proportional to the log of the size of the phage DNA and allowed selection of phage carrying inserted IFN DNA of size of 1000 to 1200 base pairs. Double-stranded RF1 DNA was prepared from the phage by the method of Moses et al. [Moses, P. B., Boeke, J. D., Horuchi, K. and Zinder, N. D., Virology 104, 267-273 (1980)]. This DNA was cut with HindIII restriction endonuclease and the resulting fragments analyzed on an agarose gel to confirm that the insert was in the HindIII site and of the anticipated size. One of the phage DNA's which has an insert of about 1200 base pairs (bp) was chosen for further study. The DNA insert was sequenced by the method of Maxam and Gilbert [Maxam, A. M. and Gilbert, W., Methods in Enzymol 68, 499-560 (1980)].

6. Expression of LeIFN in Saccharomyces cerevisiae

Figure 5:
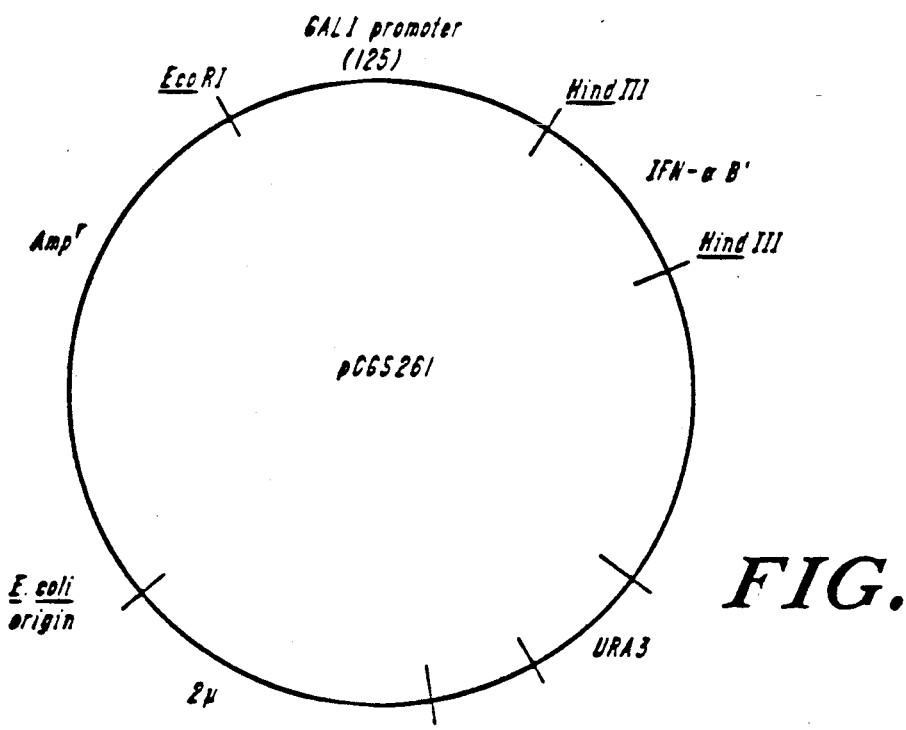
FIG. 5 is a diagrammatical showing of pCGS261.

A plasmid, pCGS261, as seen in FIG. 5, designed to facilitate obtaining expression of LeIFN in yeast was constructed. In order to produce the LeIFN in yeast, an ATG initiation codon was incorporated at the 5'-side of the first codon (TGT for cysteine) of mature, processed IFN. Based on the fact that Sau3AI cuts at the 3'-side of the first codon, an oligonucleotide (ACACATC-GATGTGT) which is recognized by ClaI and also contains the ATG-TGT sequence was synthesized by Collaborative Research, Inc. A Sau3AI fragment which codes the amino acid residues 2 to 61 was purified by digesting 30 µg of the HindIII 1.2 kilobase fragment with 10 units Sau3AI restriction endonuclease in a 50 µl reaction volume containing 10 mM Tris-HCl, pH 7.5; 10 mM $MgCl_2$; and 60 mM NaCl for 4 hours at 37° C. The DNA fragment was purified by polyacrylamide gel electrophoresis. The DNA was phenol extracted and precipitated with ice-cold absolute ethanol. The cohesive ends were filled in by treating the DNA with 4 units E. coli DNA Polymerase I Klenow fragment with 0.1 mM each nucleoside triphosphate in 66 mM Tris-HCl, pH 7.5; 66 mM NaCl; 66 mM $MgCl_2$ and 66 mM dithiothreitol, for 30 minutes at room temperature.

The above synthetic oligonucleotide was ligated onto the Sau3AI fragment in 66 mM Tris-HCl, pH 7.5; 10 mM $MgCl_2$; 10 mM 2-mercaptoethanol; 1 mM ATP with 500 pmole $^{32}$P-oligonucleotide (5 µg); 4 pmoles DNA (20 µg) and 4 blunt-end units of T4 DNA ligase at 17° C. overnight. This ligation created an ATG initiation codon and restored the first codon TGT. ClaI polylinker was removed by treating the fragment with 20 units restriction endonuclease ClaI for 3 hours at 37° C. in a 20 µl reaction containing 10 mM Tris-HCl, pH 7.5; 10 mM $MgCl_2$; and 1 mg/ml bovine serum albumin. The resulting fragment was cloned into the ClaI site of plasmid pBR322. The plasmid (10 µg) was cut with the restriction endonuclease ClaI (New England Biolabs, 20 units) for 2 hours at 37° C. in a 20 µl reaction containing 10 mM Tris-HCl, pH 7.5; 10 mM $MgCl_2$ and 1 mg/ml bovine serum albumin. The preparation of restriction cut plasmid was phenol extracted, ethanol precipitated and treated with calf intestinal phosphatase by the method of H. Goodman and R. J. MacDonald [Goodman, H. M. and MacDonald, R. J., *Methods in Enzymology* 68, 75–91 (1979)] to remove the terminal phosphates. Approximately 0.5 pmole of the ClaI fragment and 0.3 pmole of the ClaI cut plasmid were ligated together at 15° C. for 3 hours in a 20 µl reaction containing 66 mM Tris-HCl, pH 7.5; 6 mM $MgCl_2$; 10 mM dithiothreitol; 1 mM ATP; and T4 DNA ligase (New England Biolabs, 300 units) creating plasmid pCGE32. Transformation-competent E. coli strain CGE43 (LG90; F$^-$Δ(lac-pro)xlll) was prepared as described previously for CGE6, and 5 µl of the ligated DNA was mixed with 200 µl of the cells for 30 minutes at 0° C., heat treated at 37° C. for 2 minutes, incubated at 18° C. for 10 minutes, and diluted five-fold with fresh tryptone broth. After incubation for 30 minutes at 37° C. with shaking, cells were plated on tryptone plates containing ampicillin (20 µg/ml). Ampicillin-resistant colonies were picked, and the plasmid DNA was prepared and analyzed by restriction enzyme digestion. By these criteria several cells carried the desired plasmid, pCGE32.

The rest of the IFN gene was put back together by using the EcoRI site located in the region coding for amino acid residue 37. Plasmid pCGE32 DNA (10 µg) was cut with the restriction endonuclease HindIII (Collaborative Research, Inc., 12 units) for 2 hours at 37° C. in a 20 µl reaction containing 10 mM Tris-HCl, pH 7.5; 10 mM $MgCl_2$; 60 mM NaCl; and 1 mg/ml bovine serum albumin). This DNA was next digested with the endonuclease EcoRI (Collaborative Research, Inc., 15 units) for 3 hours at 37° C. in a 20 µl reaction containing 100 mM Tris-HCl, pH 7.6; 10 mM $MgCl_2$; 30 mM NaCl; and 1 mg/ml bovine serum albumin. The restriction cut DNA was phenol extracted, ethanol precipitated, redissolved in water and applied to a preparative horizontal 1.5% agarose gel. After electrophoresis for 2 to 3 hours in 40 mM Tris-acetate, pH 7.2, the gel was stained with ethidium bromide and examined under long wavelength ultraviolet light. The digested HindIII to EcoRI band which codes the ATG-TGT to amino acid residue 37 was excised and the DNA extracted by freezing and thawing the gel pieces [Thuring, et al., *Anal. Biochem* 66, 213 (1975)]. The DNA fragment was ethanol-precipitated and redissolved in water. The plasmid (20 µg) containing the IFN clone was cut with the restriction endonuclease HindIII (New England Biolabs, 180 units) for 2 hours at 37° C. as above and then the DNA (12 µg) was cut with the restriction endonuclease EcoRI (New England Biolabs, 24 units) for 6 minutes at 37° C. The restriction cut DNA was phenol extracted, ethanol precipitated, and redissolved in water. This EcoRI to HindIII fragment coding for amino acid residue 37 to the 3'-nontranslating region of IFN was analyzed by gel electrophoresis and excised from the gel (see above). Approximately 0.25 pmole of each fragment were ligated together into plasmid pBR322 opened at its HindIII site (see above) for 4 hours at 14° C. in a 20 µl reaction containing 66 mM Tris-HCl, pH 7.6; 6.6 mM $MgCl_2$; 10 mM dithiothreitol; 1 mM ATP and T4 DNA ligase (New England Biolabs, 300 units). Transformation-competent E. coli strain CGE43 cells were prepared exactly as described above, and 5 µl of the ligated DNA was mixed with 100 µl of the cells for 30 minutes at 0° C., heat treated at 37° C. for 2.5 minutes, and diluted ten-fold with fresh tryptone broth. After incubation for 30 minutes at 37° C. with shaking, cells were plated on tryptone plates containing ampicillin (20 µg/ml). Ampicillin-resistant colonies were picked, and the plasmid DNA was prepared and analyzed by restriction enzyme digestion. By these criteria several strains carried the desired plasmid, pCGE38.

A HindIII site was constructed in pCGS109 which is a standard shuttle vector (pCGS42) with $P_{GAL1}$ inserted between the EcoRI and BamHI sites. The vector, pCGS109, was cut with BamHl restriction enzyme, digested with Sl nuclease to remove cohesive ends making it blunt-ended and then ligating on HindIII linker. The vector was treated with HindIII restriction enzyme and then the cohesive ends were ligated together to produce the vector pCGS135. The 1.1 kilobase HindIII fragment containing the gene for LeIFN was isolated from plasmid pCGE38 (30 µg) by cutting the plasmid with restricton endonuclease HindIII for 1.5 hours at 37° C. as above. The restriction cut DNA was phenol extracted, ethanol precipitated, redissolved in water and applied to a preparative 1% agarose gel. After electrophoresis in 40 mM Tris-acetate, pH 7.2, the gel was stained with ethidium bromide and examined under long wavelength ultraviolet light. The 1.1 kilobase band was excised and the DNA extraced by freezing and thawing the gel pieces [Thuring, et al., *Anal. Biochem.* 66, 213 (1975)]. The DNA fragment was ethanol precipitated and redissolved in water. Approximately 0.2 µg of the HindIII fragment was ligated into plasmid pCGS135 (1 µg) opened at its HindIII site adjacent to the $P_{GAL1}$ region. Ligation of the vector and IFN fragment was carried out at 14° C. in a 20 µl reaction containing 66 mM Tris-Hcl, pH 7.6; 6.6 mM $MgCl_2$; 10 mM dithiothreitol; 1 mM ATP and T4 DNA ligase (Collaborative Research, Inc., 10 units).

The yeast strain CGY528 (αura 3-52, his 4-29, pep 4-3, GAL+) was transformed with the plasmid DNA by the method of A. Hinnen, J. B. Hicks, and G. Fink [Hinnen, A., Hicks, J. B. and Fink, G. F., *Proc. Nat. Acad. Sci. USA* 75, 1929-1933 (1978)]. Yeast transformant CGY528, capable of growth without added uracil due to the presence of URA3 gene on the plasmid was picked. (Strain CGY528 bearing plasmid pCGS261 is on deposit with the American Type Culture Collection (ATCC), Accession Number 20663, deposited February, 1983.) The yeast cells were grown at 30° C. with agitation in a medium containing 6.7 g/l yeast nitrogen base, 20 µg/l histidine and 2% galactose. The synthesis of interferon was verified by collecting cells grown to Klett = 50 ($10^7$ cells/ml) by centrifugation, resuspended in 0.25 ml 0.05M Tris-HCl, pH 7.6, 20% glycerol and 1 mM PMSF, and frozen at −20° C. The cells were disrupted by glass beads by the method of M Rose, et al. [Rose, M., Casadaban, M. J. and Botstein, D., *Proc. Nat. Acad. Sci. USA* 78, 2460-2464 (1981)] and the amount of interferon activity in the cellular extract was determined by conventional methods to be $10^5$ units/mg of soluble protein.

The sequencing information for the human leukocyte interferon gene produced is shown in Table 3.

TABLE 3

```
CAAGCTTG  GTC  ATCCATCTGA  ACCAGCTCAG  CAGCATCCAC  AACATCTACA  ATG GCC TTG  ACT  TTT TAT TTA CTG GTG GCC CTA GTG GTG
         -40           -30          -20           -10           1          MET ALA LEU  THR  PHE TYR LEU LEU VAL ALA LEU VAL VAL
                                                                             1                                              10

40              50              60              70              80              90             100             110             120
CTC AGC TAC AAG TCA TTC AGC TCT CTG  GGC  TGT GAT CTG CCT CAG ACT CAC AGC  CTG GGT AAC AGG AGG GCC TTG ATA CTC
LEU SER TYR LYS SER PHE SER SER LEU  GLY  CYS ASP LEU PRO GLN THR HIS SER  LEU GLY ASN ARG ARG ALA LEU ILE LEU
              20                                        30                                40

130             140             150             160             170             180             190             200
CTG GCA CAA ATG CGA AGA AGA ATC TCT CCT  TTC TCC TGC CTG AAG GAC AGA CAT GAC  TTT GAA TTC CCC CAG GAG TTT GAT
LEU ALA GLN MET ARG ARG ARG ILE SER PRO  PHE SER CYS LEU LYS ASP ARG HIS ASP  PHE GLU PHE PRO GLN GLU PHE ASP
              50                                        60

210             220             230             240             250             260             270             280
GAT AAA CAG TTC CAG AAG GCT CAA GCC  ATC TCT GTC CTC CAT GAG ATG ATC CAG  CAG ACC TTC AAC CTC TTC AGC ACA AAG
ASP LYS GLN PHE GLN LYS ALA GLN ALA  ILE SER VAL LEU HIS GLU MET ILE GLN  GLN THR PHE ASN LEU PHE SER THR LYS
              70                                        80                                90

290             300             310             320             330             340             350             360
GAC TCA TCT GCT GCT TTG GAT GAG ACC  CTT CTA GAT GAA TTC TAC AAT GAA CTT  GAC  CAG CAG CTG AAT GAC CTG GAG TCC
ASP SER SER ALA ALA LEU ASP GLU THR  LEU LEU ASP GLU PHE TYR ILE GLU LEU  ASP  GLN GLN LEU ASN ASP LEU GLU SER
             100                                       110                                120

370             380             390             400             410             420             430             440
TGT GTG ATG CAG GAA GTG GGG GTG ATA  GAG TCT CCC CTG ATG TAC GAG GAC TCC  ATC CTG GCT GTG AGG AAA TAC TTC CAA
CYS VAL MET GLN GLU VAL GLY VAL ILE  GLU SER PRO LEU MET TYR GLU ASP SER  ILE LEU ALA VAL ARG LYS TYR PHE GLN
             130                                                                          140

450             460             470             480             490             500             510             520
AGA ATC ACT CTA TAT  CTG ACA GAG AAG  AAA TAC AGC TCT TGT GCC TGG GAG GTT  GTC AGA GCA GAA ATC ATG AGA TCC TTC
ARG ILE THR LEU TYR  LEU THR GLU LYS  LYS TYR SER SER CYS ALA TRP GLU VAL  VAL ARG ALA GLU ILE MET ARG SER PHE
             150                                       160                                170

530             540             550             560             570             580             590             600             610
TCT TTA TCA ATC AAC TTG CAA AAA AGA  TTG AAG AGT AAG GAA TGA GACCTGGTAC  AACACGGAAA TGATTCTTAT AGACTAATAC
SER LEU SER ILE ASN LEU GLN LYS ARG  LEU LYS SER LYS GLU
             180

620        630        640        650        660        670        680        690        700        710
AGCAGTCAC ACTTCGACAA GTTGTGCTCT TTCAAAGACC CTTGTTTCTG CCAAAAACCAT GCTATGAATT GAATCAAATG TGTCAAGTGT TTTCAGGAGT 720        730        740        750        760        770        780        790        800        810
GTTAAGCAAC ATCCTGTTCA GCTGTATGGG CACTAGTCCC TTACAGATGA CCATGCTGAT GGATCTATTC ATCTATTTAT TTAAATCTTT ATTTAGTTAA 820        830        840        850        860        870        880        890        900        910
CTATCTATAG GGCTTAAATT AGTTTTGTTC ATATTATATT ATGTGAACTT TTATATTGTG AATTGTGTAA CAAAAACATG TTCTTTATAT TTATTATTTT 920        930        940        950        960        970        980        990        1000       1010
GCCTTGTTTA TTAAATTTTT ACTATAGAAA AATTCTTTTA AAATTGAACT CCAACCCTGA TTGTGCAAAC TGATTAAAGG AAGTGGTGCA 1020       1030       1040       1050       1060       1070       1080       1090       1100       1110
CTTGCAAACA AGCTCTACTA TCCCTGAGGA AATACCAGAG ACTCTGGAAG GTGATATTCA AAAAGCAAAA AGCAAAATTC TAACACTAAT TGAACCTGAC
```

TABLE 3-continued

| 1120 | 1130 | 1140 | 1150 | 1160 | 1170 | 1180 | 1190 |
|---|---|---|---|---|---|---|---|
| ATTAAAACAG | CACAGATGAC | TGCTACCATA | GATTCCTGCC | TTTCAAACGC | AGGGCAAGAC | ATTCATTGGT | CATACGTAGA AGGC <u>CAAGCTTG</u> |

EXAMPLE 3

Production of Prorennin

1. Isolation of the RNA

Stomach tissue from milk-fed calves was obtained fresh from a local slaughterhouse; the mucosa of the fourth stomach was dissected away from the stomach wall and frozen in dry ice. Twenty-one grams of the mucosal tissue was disrupted by means of a blender into 200 ml of cold buffer (10 degrees C.) consisting of 50mM Tris.HCl, PH 7.5, 8M guanidine HCl, and 1 mM dithiothreitol. Insoluble material was removed by centrifugation in a Sorvall SA-600 rotor at 10,000 rpm for 12 minutes. To the 200 ml of supernatant from the spin was added 100 ml of ice cold absolute ethanol. After 1.5 hours at −20 degrees C., the precipitate was pelleted by a centrifugation at 3000 rpm for 30 minutes at −10 degrees C. The pellet was dissolved in 40 ml of ice cold buffer (EGAD) consisting of 20 mM EDTA, pH7, 20 mM NaOAc, pH7, 8M guanidine.HCl, and 1 mM dithiothreitol. Twenty milliliters of cold absolute ethanol was added and the solution placed at −20 degrees C. for 45 minutes. The precipitate was pelleted by centrifugation at 3000 rpm for 20 minutes at −10 degrees C. The pellet was redissolved in 40 ml cold EGAD buffer and the precipitation with 20 ml cold ethanol, centrifugation and redissolving the pellet in EGAD buffer was repeated two additional times. Finally, the pellet was dissolved in 16 ml of 20 mM EDTA, pH 7 and extracted three times with chloroform:isobutanol (4:1). Next, two volumes of 4.5M NaOAc pH5.2 was added to the aqueous layer and the solution was placed at −20 degrees C. overnight. The RNA precipitate was collected by centrifugation at 10,000 rpm for 25 minutes at −10 degrees C., and was dissolved in 30 ml water. The yield was 45 mg RNA. The RNA was precipitated by addition of 1 ml of 2M NaOAc pH5 and 75 ml absolute ethanol, followed by incubation at −20 degrees C. overnight. The RNA was pelleted by centrifugation (10,000 rpm, 10 minutes −10 degrees C.) and redissolved in 20 ml water, heated to 60 degrees C. for 10 minutes, chilled rapidly on ice and diluted with 21 ml of 2× concentrated binding buffer (20 mM Tris.HCl pH7.5, 2 mM EDTA pH7, 0.4% SDS and 0.24M NaCl). The RNA was applied to a 4 ml oligo-dT-cellulose column, the column was washed with 45 ml of 1× concentrated binding buffer, and then the poly A-containing RNA was eluted by washing the column with binding buffer containing no NaCl. About 1 mg of poly A-containing RNA was obtained. A portion of the poly A-containing RNA was translated in vitro in a rabbit reticulocyte lysate system (H. R. B. Pelham and R. J. Jackson [1976] *Eur J. Biochem.* 67 247–256). The protein products were analyzed on a 10% polyacrylamide gel. A single major protein band was observed which was precipitated with rennin antiserum showing that rennin mRNA is present in the poly A-containing RNA.

2. Preparation of double-stranded copy DNA (cDNA)

About 8.7 µg of cDNA was synthesized from 20 µg of the calf stomach poly A-containing RNA by incubation for one hour at 42 degrees C. in 50 mM Tris.HCl pH8.3, 100 mM KCl, 8 mM MgCl$_2$, 0.4 mM dithiothreitol, 1 mM each deoxynucleoside triphosphate, 20 µg/ml oligo(-dT)$_{12-18}$ containing 100 units reverse transcriptase and 1 Ci/mmole $\alpha^{32}$P-dCTP. After heating the reaction mixture at 100 degrees C. for 3 minutes, chilling on ice for 3 minutes and removing the precipitated protein by centrifugation, to half the supernatant material was added Hepes.KOH pH6.9 to 100 mM, MgCl$_2$ to 5 mM, dithiothreitol to 0.5 mM, deoxynucleoside triphosphates to 0.125 mM. Incubation of this mixture with 300 units of *E. coli* DNA polymerase I for 2 hours at 16° C. produced 8.6 µg of double-stranded cDNA. The DNA was phenol extracted and separated from unincorporated triphosphates by chromatography on Sephadex G-100 (12 ml column, 0.7 cm×30 cm, eluted with 20 mM Tris.HCl pH 7.5, 0.5 mM EDTA) and was ethanol precipitated overnight at −20 degrees C. by addition of 1/10 volume 2M NaOAc pH5, and 2.5 volumes cold ethanol. The double-stranded cDNA (4.6 µg) was then treated with 1000 units of S1 nuclease at 37 degrees C. for 1 hour in Buffer S (0.3M NaCl, 30 mM NaOAc, pH4.6, 3 mM ZnSO$_4$) The reaction was terminated by addition of EDTA to 10 mM, and Tris.HCl pH8.3 to 200 mM, and the mixture applied to a Biogel A-150m column (0.7 cm×33 cm) equilibrated and eluted with 10 mM Tris.HCl pH7.5, 1 mM EDTA and 250 mM NaCl. The peak fractions (0.5 ml each) of large molecular weight DNA were pooled and ethanol precipitated by addition of 1/10 volume 2M NaOAC pH5 and 2.5 volumes cold absolute ethanol.

3. Addition of HindIII Linkers

The S1-treated double-stranded cDNA (1.7 µg) was incubated in Buffer T (25 mM Tris.HCl pH8, 6.6 mM MgCl$_2$, 0.5 mM EDTA, 5 mM 2-mercaptoethanol and 0.5 mM of each deoxynucleoside triphosphate) with 2 units of T$_4$ DNA polymerase at room temperature for 30 minutes. The material was phenol extracted and ether extracted and ethanol precipitated by addition of 1/10 volume 2M NaOAc pH5 and 2.5 volumes ethanol. This blunt-ended double-stranded cDNA was next incubated in 66 mM Tris.HCl pH7.6, 6.6 mM MgCl$_2$, 5 mM 2-mercaptoethanol, 0.5 mM ATP, with 300 pmoles of $_{32}$P-labelled Hind III synthetic linker (100×excess over cDNA ends) and 9 blunt-end units of T$_4$ DNA ligase at 12 degrees overnight.

The reaction was adjusted to 10 mM EDTA pH8 and fractionated on a Biogel A-150m column (0.7 cm×20 cm). Fractions (0.25 ml each) containing high molecular weight DNA were pooled and ethanol precipitated. This material was treated with Hind III restriction endonuclease (9 units) in 5.6 mM Tris.HCl pH7.6, 5.6 mM MgCl$_2$ at 37 degrees C. for 45 minutes, then phenol extracted, ether extracted and ethanol precipitated by the addition of 1/10 volume 1M NaOAc pH5 and 2.5 volume, absolute ethanol. This double-stranded cDNA with Hind III cohesive termini was then ligated to f1 phage CGF4 double-stranded DNA which had been cut open with Hind III restriction endonuclease and treated twice with calf intestinal phosphatase by the method of H. Goodman and R. J. MacDonald (H. M. Goodman and R. J. MacDonald [1979] *Methods in Enzymology* 68, 75–91) to remove the terminal phosphates (Note: In order to produce phage CGF4, f1 phage R229 (J. D. Boecke [1981] *Mol. Gen. Genet.* 181, 288–291) was cut with EcoRI endonuclease, rendered blunt-ended with T4 DNA polymerase and ligated with Hind III synthetic oligonucleotide linkers from Collaborative Research, Inc. of Waltham, Mass.). The ligation reaction contained 66 mM Tris.HCl pH7.6, 6.6 mM MgCl$_2$, 5 mM 2-mercapto-ethanol, 0.3 µg double-stranded cDNA, 0.2 µg CGF4 DNA, 0.5 mM ATP and 300 cohesive-end units of T$_4$ DNA ligase. Ligation was for 29 hours at 16 degrees C.

4. Transfection of E. coli BNN45 with recombinant-CGF4 DNA

E. coli strain CGE6 (BNN45; hsdR⁻, hsdM⁺, sup E, sup F, Bl⁻, met⁻) was grown in tryptone broth at 37 degrees C. with shaking and harvested at $OD_{700}=0.5$ by centrifugation at 7000 rpm for 10 minutes at 4 degrees C. The cells were resuspended in ice cold 50 mM $CaCl_2$ (one-half the original culture volume) and allowed to sit at 0 degrees C. for 30 minutes. The suspension was then centrifuged at 7000 rpm for 10 minutes at 4 degrees C. and resuspended in 1/20 the original culture volume ice cold 50 mM $CaCl_2$. After standing at 0 degrees C. for 60 minutes the cells were used for transfection. One-half microliter of the 20 µl ligation reaction was added to each of 8 tubes containing 50 µl sterile 50 mM Tris.HCl pH7.6. One-tenth milliliter of the $CaCl_2$-treated cells was added to each tube and the mixtures sat on ice for 30 minutes. After warming to 37° C. for two minutes, 0.2 ml of a CGE5(JM101: J. Messing [1979], F'tra D36 pro AB lac IZ∇M15 in a ∇(lac pro) SupEthi⁻ background) overnight culture and 3 ml of 0.7% soft agar were added, and the mixture poured onto eight tryptone agar plates. Incubation at 37 degrees C. overnight produced about 250 plaques per plate.

5. Identification of a Recombinant CGF4 carrying the rennin coding sequence

The plaques were transferred to nitrocellulose and probed as described by Benton & Davis (W. D. Benton and R. W. Davis [1977] *Science* 196, 180–182) using $^{32}P$-labelled cDNA made from the calf-stomach poly A-containing RNA using $\alpha^{32}P$-dCTP and reverse transcriptase (T. P. St. John and R. W. Davis [1979] *Cell* 16 443–452). About 80 recombinant phage which hybridize intensely to the labelled cDNA were picked from the plates and stored in TY medium at 4 degrees C. Samples of the intact phage were amplified by growth overnight on CGE5 cells, harvested by centrifugation, and subjected to electrophoresis in a 2% agarose gel containing 0.37M Tris.glycine pH9.5 and stained with ethidium bromide after treatment in 0.2N NaOH for one hour and neutralization in 0.5M Tris.HCl pH7.4. The migration is inversely proportional to the log of the size of the phage DNA and allowed selection of eight phage carrying inserted DNA of size 1000 to 2000 base pairs. Double-stranded RFI DNA was prepared from these eight phages by the method of Moses et al (P. B. Moses, J. D. Boeke, K. Horiuchi & N. D. Zinder [1980] *Virology* 104, 267). This DNA was cut with Hind III and the resulting fragments analyzed on an agarose gel to confirm that the insert was in the Hind III site and of the anticipated size. Finally, the DNA from four of the recombinant phages (approximately 5–10 µg from each) and DNA from the vector CGF4 was cut with Hind III and the fragments, after denaturation by boiling for 45 seconds and freezing in dry ice/ethanol, were bound to nitrocellulose by spotting the DNA in water onto small pieces of nitrocellulose pretreated with 20x SSC and dried. After baking in vacuo at 75 degrees C. for 1.5 hours, the DNA bound to nitrocellulose was carried through the hybrid selection procedure as described by Miller et al (J. S. Miller, R. P. Ricciardi, B. E. Roberts, B. M. Paterson & M. B. Mathews [1980] *J. Mol. Biol.* 142, 455–488) using 2 µg poly A-enriched calf stomach RNA for each hybridization. The eluted RNA was then translated in a reticulocyte lysate system labelling with $^{35}S$-methionine by the method of Pelham and Jackson (H. R. B. Pelham & R. J. Jackson [1976] *Eur. J. Biochem.* 67, 247–256) and the resulting protein products analyzed on a 10% polycrylamide gel containing 0.1% SDS according to Laemmli (U. Laemmli [1970]*Nature* 227, 680–685). The results of the gel analysis indicated that all four of the phage DNAs tested did hybridize to the rennin mRNA since all four selected an RNA species which, upon translation in a rabbit reticulocyte lysate, yields a protein product identical to pre-prorennin in size and immunological criteria. Two of the four, 293-207 which has an insert of about 1400 base pairs (bp) and 293-118/37 which has an insert of about 1250 bp, were chosen for further study. The DNA inserts were sequenced by the method of Maxam and Gilbert (A. M. Maxam and W. Gilbert [1980] *Methods in Enzymology* 68, 499–560). From nucleotide 205 to 1350 is the DNA sequence for the pre-prorennin A gene (see Table 4). The nucleotide sequences 1–204 and 1351 to 1460 are attached to the pre-prorennin but can be removed if desired and are not essential to use of the gene in expression. Useful portions of the DNA material of Table 4 can be separated and used by known techniques.

TABLE 4

| | 30 | | 60 | | 90 |
|---|---|---|---|---|---|
| AAG CTT GGG CGA GCG AGG GGT AGG CCA TCC | | CCA GGA TCC CGT CGA ATT CGG CAT AGG TGA | | AGA CGT CCC CGG GCT CCT GGG TGC TCA GGC | |
| | 120 | | 150 | | 180 |
| CTA CTG TCT GCT GGA TGT CCA CAA TGT TGG | | AGA CAG TGA CGG TGT CAT AGC CCA GGA TGC | | CCT GCA TGC TGC CTG TCC CGT AGT GGA TAG | |
| | 210 | | 240 | | 270 |
| ACA GCG GCT GGA CCC AGA TCC AAG ATG AGG<br>MET ARG | | TGT CTC GTG GTG CTA CTT GCT GTC TTC GCT<br>CYS LEU VAL VAL LEU LEU ALA VAL PHE ALA | | CTC TCC CAG GGC GCT GAG ATC ACC AGG ATC<br>LEU SER GLN GLY ALA GLU ILE THR ARG ILE | |
| | 300 | | 330 | | 360 |
| CCT CTG TAC AAA GGC AAG TCT CTG AGG AAG<br>PRO LEU TYR LYS GLY LYS SER LEU ARG LYS | | GCG CTG AAG GAG CAT GGG CTT CTG GAG GAC<br>ALA LEU LYS GLU HIS GLY LEU LEU GLU ASP | | TTC CTG CAG AAA CAG CAG TAT GGC ATC AGC<br>PHE LEU GLN LYS GLN GLN TYR GLY ILE SER | |
| | 390 | | 420 | | 450 |
| AGC AAG TAC TCC GGC TTC GGG GAG GTG GCC<br>SER LYS TYR SER GLY PHE GLY GLU VAL ALA | | AGC GTG CCC CTG ACC AAC TAC CTG GAT AGT<br>SER VAL PRO LEU THR ASN TYR LEU ASP SER | | CAG TAC TTT GGG AAG ATC TAC CTC GGG ACC<br>GLN TYR PHE GLY LYS ILE TYR LEU GLY THR | |
| | 480 | | 510 | | 540 |
| CCG CCC CAG GAG TTC ACC GTG CTG TTT GAC<br>PRO PRO GLN GLU PHE THR VAL LEU PHE ASP | | ACT GGC TCC TCT GAC TTC TGG GTA CCC TCT<br>THR GLY SER SER ASP PHE TRP VAL PRO SER | | ATC TAC TGC AAG AGC AAT GCC TGC AAA AAC<br>ILE TYR CYS LYS SER ASN ALA CYS LYS ASN | |
| | 570 | | 600 | | 630 |
| CAC CAG CGC TTC GAC CCG AGA AAG TCG TCC<br>HIS GLN ARG PHE ASP PRO ARG LYS SER SER | | ACC TTC CAG AAC CTG GGC AAG CTG AAG CCC TCT<br>THR PHE GLN ASN LEU GLY LYS LEU LYS PRO LEU SER | | ATC CAC TAC GGG ACA GGC AGC ATG CAG GGC<br>ILE HIS TYR GLY THR GLY SER MET GLN GLY | |
| | 660 | | 690 | | 720 |
| ATC CTG GGC TAT GAC ACC GTC ACT GTC TCC<br>ILE LEU GLY TYR ASP THR VAL THR VAL SER | | AAC ATT GTG GAC ATC CAG CAG ACA GTA GGC<br>ASN ILE VAL ASP ILE GLN GLN THR VAL GLY | | CTG AGC ACC CAG GAG CCC GGC GAC GTC TTC<br>LEU SER THR GLN GLU PRO GLY ASP VAL PHE | |
| | 750 | | 780 | | 810 |
| ACC TAT GCC GAA TTC GAC GGG ATC CTG GGG<br>THR TYR ALA GLU PHE ASP GLY ILE LEU GLY | | ATG GCC TAC CCC TCG CTC GCC TCA GAG TAC<br>MET ALA TYR PRO SER LEU ALA SER GLU TYR | | TCG ATA CCC GTG TTT GAC AAC ATG ATG AAC<br>SER ILE PRO VAL PHE ASP ASN MET MET ASN | |
| | 840 | | 870 | | 900 |
| AGG CAC CTG GTG GCC CAA GAC CTG TTC TCG<br>ARG HIS LEU VAL ALA GLN ASP LEU PHE SER | | GTT TAC ATG GAC AGG AAT GGC GAG GAG ACC<br>VAL TYR MET ASP ARG ASN GLY GLU GLU THR | | ATG CTC ACG CTG GGG GCC ATC AGC GAC CCG TCC<br>MET LEU THR LEU GLY ALA ILE ASP PRO SER | |
| | 930 | | 960 | | 990 |
| TAC TAC ACA GGG TCC CTG CAC GAC CTG GTG CCC<br>TYR TYR THR GLY SER LEU HIS ASP LEU VAL PRO | | GTG ACA GTG CAG CAG TAC TCC AAG TTC CAG TTC ACT<br>VAL THR VAL GLN GLN TYR SER LYS PHE GLN PHE THR | | GTG GAC AGT GTC ACC ATC AGC GGT GTT<br>VAL ASP SER VAL THR ILE SER GLY VAL VAL | |
| | 1020 | | 1050 | | 1080 |
| GTG GCC TGT GAG GGT GGC TGT CAG GCC ATC<br>VAL ALA CYS GLU GLY GLY CYS GLN ALA ILE | | CTG GAC ATC GAC GGC ACC TCC AAG CTG GTC GGG<br>LEU ASP ILE ASP GLY THR SER LYS LEU VAL GLY | | CCC AGC AGT GAC ATC AAC ATC AGC AGC<br>PRO SER SER ASP ILE LEU ASN ILE GLN GLN | |
| | 1110 | | 1140 | | 1170 |
| GCC ATT GGA GCC ACA CAG AAC CAG TAC GAT<br>ALA ILE GLY ALA THR GLN ASN GLN TYR ASP | | GAG TTT GAC ATC GAC TGC GAC AAC CTG AGC<br>GLU PHE ASP ILE ASP CYS ASP ASN LEU SER | | TAC ATG CCC ACT GTG GTC TTT GAG ATC AAT<br>TYR MET PRO THR VAL VAL PHE GLU ILE ASN | |
| | 1200 | | 1230 | | 1260 |
| GCC ATT GGA GCC ACA CAG AAC CAG TAC GAT<br>GLY LYS MET TYR CCA CTG ACC CCC TCC GCC<br>GLY LYS MET TYR PRO LEU THR PRO SER ALA | | TAT ACC AGC GAC CAG GAC CAG GGC TTC TGT ACC<br>TYR THR SER GLN ASP GLN GLY PHE CYS THR | | AGT GGC TTC CAG AGT GAA AAT CAT TCC CAG<br>SER GLY PHE GLN SER GLU ASN HIS SER GLN | |

TABLE 4-continued

| | | |
|---|---|---|
| 1290 | 1320 | 1350 |
| AAA TGG ATC CTG GGG GAT GTT TTC ATC CGA | GAG TAT TAC AGC GTC TTT GAC AGG GCC AAC | AAC CTC GTG GGG CTG GCC AAA GCC ATC TGA |
| LYS TRP ILE LEU GLY ASP VAL PHE ILE ARG | GLU TYR TYR SER VAL PHE ASP ARG ALA ASN | ASN LEU VAL GLY LEU ALA LYS ALA ILE |
| 1380 | 1410 | 1440 |
| TCA CAT CGC TGA CCA AGA ACC TCA CTG TCC | CCA CAC ACC TGC ACA CAC ACA TGC ACA CAT | GTA CAT GGC ACA TGT GCA CAC ACA CAG ATG |
| AGG TTT CCA GAC CCA AGC TT | | |

This table combines information from both 293-207 and 293-118/37: recombinant phage 293-207 carries an insert bearing the sequence shown in Table 4 from nucleotide #1 to at least nucleotide #1360 except for nucleotides 848-961 which are deleted, while phage 293-118/37 carries an insert bearing the sequence from nucleotide #229 to nucleotide #1460. As revealed by the sequencing results, initiation of rennin synthesis occurs at a methionine codon (nucleotides 205-207) and results in a pre-prorennin molecule with sixteen additional amino acids compared to purified prorennin (The prorennin B amino acid sequence was published by B. Foltmann et al. *Proc. Nat. Acad. Sci. USA* 74 2321-2324(1977) and B. Foltmann et al *J. Biol. Chem.* 254 8447-8456 (1979); the nucleotide sequencing data of Table 4 is the first indication for the existence of pre-prorennin). Together, the two recombinant f1 phages 293-207 and 293-118/37 carry the DNA sequence for the entire pre-prorennin A molecule. The prorennin portion of the pre-prorennin A differs from prorennin B at amino acid #290 (aspartate in rennin A and glycine in rennin B as described by Foltmann et al [see above]; amino acid position numbering is that of Foltmann). An asparagine codon is shown at amino acid position #204 while Foltmann reported an aspartate at that position; however, this may be an amino acid sequencing error since the amides of aspartate and glutamate are difficult to distinguish from their acid forms, while nucleotide sequencing can readily distinguish the codons.

The cloned rennin gene represented by phage 293-118/37 was used to investigate properties of the bovine genomic copy or copies of the rennin gene. These experiments were done by hybridizing cloned rennin DNA labelled with $^{32}P$ by the method of nick-translation (P. W. J. Rigby, M. Dieckmann, C. Rhodes, and P. Berg [1977] *J. Mol. Biol.* 113, 237-251) to bovine DNA cut with various restriction enzymes, separated with an agarose gel and transferred to a nitrocellulose membrane according to the method of Southern (E. M. Southern [1975] *J. Mol. Biol.* 98, 503-517). The results indicate that restriction endonuclease cleavage of the bovine DNA with enzymes such as SacI and BglI, which do not cut the cloned pre-prorennin cDNA sequence, nevertheless frequently yields more than one band of DNA which will hybridize to the rennin sequence. This suggests (a) that the genomic copy of rennin information contains additional DNA, presumably intervening sequences, which contain restriction enzyme sites not found in rennin cDNA, or (b) that more than one rennin gene exists in the genome and some restriction enzymes cut between the copies. This latter possibility was eliminated by hybridizing restriction cut bovine genomic DNA with $^{32}P$-labelled probes derived from the 5' and 3' ends of the cloned rennin cDNA. These results, using restriction endonucleases EcoRI and BamHI for example, are consistent with a single genomic copy of rennin coding information. This means that A and B forms of rennin observed by B. Foltmann et al (*J. Biol. Chem.* 254, 8447-8456 [1979]) are most likely the products of two different alleles of the rennin gene. Furthermore, the bovine genomic copy of the rennin gene contains intervening sequences, and in that respect the genomic copy is different from our cloned cDNA gene which is identical to the messenger RNA for pre-prorennin.

6. Expression of Prorennin in Yeast

Recombinant f1 phage CGF 293-207 RFI DNA (40 μg) was cut with Hind III (N. E. Biolabs, 15 units) and Bgl II (N. E. Biolabs, 14 units) for one hour at 37° C. in a 103 μl reaction volume as described previously. The restriction cut DNA was applied to a preparative horizontal agarose gel, and the 435 bp 293-207 piece was excised and eluted by freezing and crushing the agarose chunk. After ethanol precipitation, the DNA was redissolved in water and about 1 μg was partially cut with HhaI (N. E. Biolabs, 0.06 units) for 15 minutes at 37° C. to obtain the 190 bp HhaI to BglII piece containing the pR start. This DNA fragment was isolated by gel as described previously and rendered blunt-ended by treatment with DNA polymerase I (Boehringer Mannheim, 14 units) in a 30 μl reaction containing 60 mM tris-HCl, pH 7.5, 8 mM $MgCl_2$, 10 mM dithiothreitol, 1 mM ATP and 0.2 mM of each deoxynucleotide triphosphate for 30 minutes at room temperature. The DNA was phenol extracted and ethanol precipitated.

A synthetic oligonucleotide bearing an Xba I restriction endonuclease sequence ending with ATGG, (i.e., CCATCTAGATGG) was synthesized by the triester method (K. Itakura, et al., *J. Biol. Chem.* 250 4592 [1975]) by Collaborative Research, Inc. and 5 μg was kinased with -p-ATP using 6 units of $T_4$ polynucleotide kinase (P-L Biochemicals) in a 35 μl reaction containing Tris HCl pH 7.6, 10 mM $MgCl_2$, 10 mM 2-mercaptoethanol and 2 nmoles ATP. This 5'-labelled oligonucleotide (22 p-moles ends) was added to about 0.5 pmoles of the 190 bp fragment with buffer plus 500 units of $T_4$ DNA ligase (N.E. Biolabs). The reaction was incubated at 15° C. for one hour then at 4° C. overnight, and then diluted with four volumes of 180 mM NaCl, 7 mM $MgCl_2$ and 5 mM Tris HCl, pH 8. After heating at 65° C. for five minutes, the DNA was treated with 12 units of XbaI restriction endonuclease (5 units additionally were added after one hour for a total of 1.5 hours of digestion). Finally, the oligonucleotide monomers were removed from the linkered 190 bp DNA by gel electrophoresis (7% polyacrylamide gel). The DNA fragment was eluted from the acrylamide chunk by soaking in buffer for 24 hours. The DNA was ethanol precipitated, redissolved in 15 μl of water and incubated in a ligation reaction containing 0.5 μg of CGF12-f1 vector opened at Xba I site and then treated With alkaline phosphatase as described previously. Aliquots of the ligation reaction were used to transform competent cells of strain LG90 as described above. The transformed cells were plated on tryptone-yeast extract plates containing f1 sensitive cells (JM101). Several phage plaques were picked and small cultures of each were grown to provide a small amount of RF1 DNA. Restriction endonuclease digestion (XbaI and HaeIII) and agarose gel electrophoresis revealed that some phage clones carried the desired 190 bp fragment in the desired orientation (5'-end of prorennin gene adjacent to the single EcoRI site of CGF12). One such isolate was named CGF21.

About 10 μg of the CGF21 DNA was cut with PstI (N. E. Biolabs, 7 units) for 45 minutes at 37° C. in a 40 ml reaction as previously described. The Pst I cut DNA was then cut with EcoRI (N.E. Biolabs, 10 units) for 45 minutes at 37° C. The 100 bp PstI/EcoRI fragment was isolated by acrylamide gel. The plasmid pBR322 (~8 μg) was cut with EcoRI (N. E. Biolabs, 7.5 units) and HindIII (N.E. Biolabs, 7.5 units) for one hour at 37° C. in a 30 μl reaction volume. The resulting HindIII/EcoRI fragment (4.3Kb) was purified by agarose gel. CGF293-118/37 DNA (10 μg) was cut with PstI (N.E. Biolabs, 8 units) and HindIII (N.E. Biolabs, 10 units) for one hour at 37° C. in a 30 μl reaction volume.

The 1.1 kb PstI/HindIII DNA fragment was purified by agarose gel. The three DNA fragments were joined in a tri-molecular ligation reaction to yield pCGE68. The tri-molecular ligation (reaction volume 27 μl) contained approximately equal molar proportions of the three fragments totaling 1.5 μg DNA. The ligation reaction was carried out with 400 units T4 DNA ligase (N.E. Biolabs) at 12° C. for 8 hours. Aliquots of the ligation reaction were used to transform competent cells of strain LE392 as described. Analysis of the plasmid DNA by restriction enzyme digestion (PstI, XbaI, BglII and KpnI) and agarose gels revealed that some isolates carried the desired plasmid pCGE68. This plasmid contains the DNA encoding Met-prorennin.

The pCGE68 DNA (10 μg) was cut with XbaI (N.E. Biolabs, 10 units for 2 hours at 37° C. After precipitation with ethanol, the DNA was rendered blunt ended by treatment with S1 nuclease (30 units) for 30 minutes at 37° C. After phenol extraction and ethanol precipitation the DNA was incubated with 5'-phosphorylated SalI linker (Collaborative Research, 2.5 μg). The linker had been kinased with γ-$^{22}$P-ATP using 2.5 units of T4 polynucleotide kinase (P-L Biochemicals) in a 10 μl reaction containing 10 mM Tris-HCl, pH 7.6, 10 mM Mg Cl$_2$ 10 mM 2-mercaptoethanol and 0.12 nmoles ATP. The linker was ligated to the blunt-ended pCGE68 DNA in a 25 μl reaction for 8 hours at 14° C. The resulting ligated DNA containing a SalI linker was used to transform competent cells of strain BNN45. Restriction enzyme (SalI) and agarose gels were used to identify the desired plasmid, pCGE91.

The construction of prorennin in yeast was now begun. The first yeast vector of interest, pCGS128, was made from a ligation of three pieces. First, pCGE91 was cut with SalI (N.E. Biolabs, 10 units) for 3 hours at 37° C. This DNA fragment was then rendered blunt-ended by treatment with DNA polymerase I (Boehringer/Mannheim, 10 units) in a 50 μl reaction containing 10 mM Tris-HCl, pH7.5, 8 mM MgCl$_2$, 10 mM dithiothreitol, and 0.2 mM of each deoxynucleotide triphosphate for one hour at room temperature. The blunt ended DNA was then ethanol precipitated, redissolved and cut with HindIII (N.E. Biolabs, 7.5 units) for 1 hour at 37° C. The 1200 bp blunt-ended SalI/HindIII DNA fragment was purified by agarose gel electrophoresis. The next DNA fragment containing the necessary components of a shuttle vector was purified from pCGS40. This latter vector was cut with EcoRI and HindIII and the resulting 7000 bp fragment was purified by agarose gel electrophoresis. The third DNA fragment containing the P$_{GAL}$promoter came from pBM125 (courtesy of R. Davis, Stanford University) which was cut with BamHI, blunted with DNA polymerase I plus all four deoxynucleotide triphosphates, then cut with EcoRI to yield a 820 bp piece designated P$_{GAL}$125. The nucleotide sequences depicting the promoter lengths are shown in Table 1. The three pieces of DNA (1200bp from pCGE91, SalI blunt-ended/HindIII, 7000 bp from pCGS 40 EcoRI/HindIII, and 820 bp from P$_{GAL}$125) were ligated together using equimolar amounts of the fragments in a 25 μl reaction containing T4 DNA ligase (Collaborative Research, 2 blunt-ended units) and appropriate buffers and ATP and incubated for 18 hours at 14° C.

The ligated DNA was used to transform competent cells of strain CGE129. Analysis of the plasmid DNA by restriction enzyme digestion and agarose gel revealed isolates which carried the desired plasmid pCGS128. DNA of pCGS128 was used to transform yeast strain CGY150. The transformed spheroplasts were selected. Western protein blot analyses revealed that the yeast strain carried prorennin (~0.02%).

In order to increase the expression of prorennin an additional construction was carried. The pCGS128 DNA was cut with HindIII. A fragment (pRB58) from the 3' end of the SUC 2 gene was cut with HindIII, made blunt-ended with E. coli DNA polymerase I and then SalI linkers were ligated on. The resulting fragment was cut with SalI and BamHI to produce a gel purified 1 kb DNA fragment which was ligated into p CGS40 cut with BamHI and SalI.

The resulting vector, pCGS108, was cut at HpaI and SalI, made blunt with E. coli DNA polymerase I and gel purified. HindIII linker (Collaborative Research, 10 nucleotides long) were ligated to the DNA fragment which was then cut with HindIII and gel purified to produce a 650 bp fragment which was ligated into the HindIII site of pCGS128 to produce pCGS168.

Figure 6:
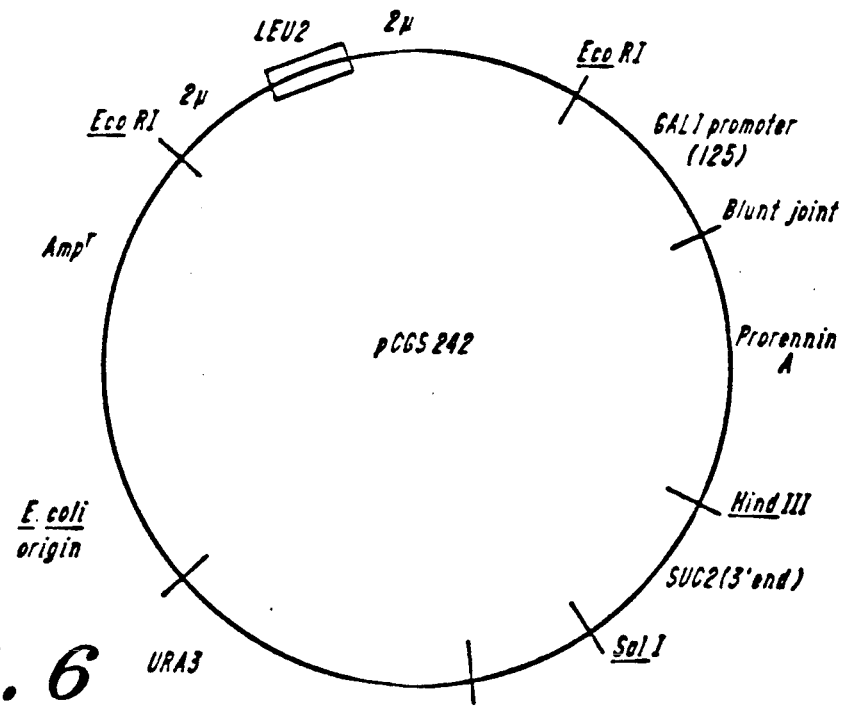
FIG. 6 is a diagrammatical showing of pCGS242.

A partial EcoRI and SalI cut was made of the pCGS168 vector to isolate a 2.6kb DNA fragment containing P$_{GAL}$125 and prorennin. A partial EcoRI cut was made from pJDB219 to produce a gel purified 2.3 kb fragment containing the LEU2 gene on a 2μ DNA fragment. These two DNA fragments were ligated together with a EcoRI/SalI digest fo Ylp5 (containing selection for URA3 to yield pCGS241 and pCGS242 (FIG. 6). The difference in structure is due to the two orientations of the 2.3 kb fragment. Both vectors were separately used to transform CGY150. Analysis of the plasmid DNA by restriction enzyme digestion and agarose gel revealed the desired plasmid with the level of prorennin expression via western analysis was increased to 0.2% of the soluble protein. The protein demonstrated milk clotting activity after conversion to rennin.

Strain CGY461 bearing plasmid pCGS242 is on deposit with the American Type Culture Collection (ATCC), Accession Number 20662, deposited February, 1983.

EXAMPLE 4

Production of Pre-prorennin

Steps 1 through 5 of Example 3 were repeated for this experiment.

6. Expression of Pre-prorennin in Yeast

Recombinant f1 phage CGF 293/207 RFI DNA (20 μg) was cut with AvaII (N.E. Biolabs, 5 units) in a 100 μl reaction. The 256 bp AvaII fragment was purified by gel electrophoresis and made blunt-ended with E. coli DNA polymerase I Klenow fragment. After phenol extraction and ethanol precipitation, the DNA was ligated with HindIII linker (Collaborative Research, CAAGCTTG) then cut with HindIII (N.E. Biolabs, 15 units) and BglII (N.E. Biolabs, 3.6 units). A 245 bp fragment was purified by gel electrophoresis containing part of the preprorennin gene. Plasmid pCGS28 DNA (U.S. patent application Ser. No. 325,481 filed Dec. 1, 1981 by B. Alford, et al.) was cut with BglII (N.E. Biolabs, 5 units) and SalI (N.E. Biolabs, 10 units) and a 1000 bp DNA fragment containing the rest of the pre-prorennin gene was purified by gel. These two DNA fragments were ligated together with pBR322 cut with HindIII (N.E. Biolabs, 12 units) and SalI (N.E. Biolabs, 8 units). This vector was used to transform competent E. coli cells and the resulting restriction enzyme analysis of plasmid DN from several *E. coli* clones revealed the desired plasmid pCGE63 in *E. coli* strain CGE130.

The preprorennin gene was used to construct PCGS148 which is p$_{GAL126}$ preprorennin. Plasmid pCGE63DNA was cut with HindIII and SalI to yield a 1200 bp fragment containing preprorennin DNA. A EcoRI/HindIII double digest was carried out on pRB118 to obtain a 850 bp fragment containing P$_{suc2}$. These fragments were ligated in a tri-molecular reaction as described with an EcoRI/SalI fragment of pCGS40 which imports the characteristics of a shuttle vector. The mixture was used to transform competent CGE129 *E. coli* cells. Clones of *E. coli* carrying the desired plasmid pCGS64 were identified by restriction digestion of plasmid DNA from several transformants. A BglII/SalI fragment (~9 kb) of pCGS64 was purified by gel electrophoresis and contained part of the preprorennin gene, as well as the pCGS40 EcoRI/SalI fragment. A BglII/Xho-I 3600 bp fragment of pCGE74 containing the rest of preprorennin fused at the SmaI site in preprorennin gene moist of the *E. coli* β-galactosidase gene was ligated to the piece from pCGS64. Transformation was carried out and restriction analyses showed the presence of the desired yeast plasmid pCGS81.

The P$_{SUC2}$ was removed from pCGS81 by restriction first with HindIII followed by filling in with *E. coli* DNA polymerase I Klenow fragment. The opened plasmid was then restricted with EcoRI and the large fragment minus P$_{suc2}$ was gel purified. The P$_{GAL126}$ was obtained by restriction of pBM126 (courtesy R. Davis, Stanford, University). The plasmid pBM126 was cut with BamHI and filled in with *E. coli* DNA polymerase 1 Klenow fragment and then cut with EcoRI to yield the desired 750 bp P$_{GAL126}$. These two fragments were ligated together to get pCGS148, which contains P$_{GAL126}$ preprorennin 'Z (where 'Z represents a portion of β-galactosidase gene).

Figure 7:
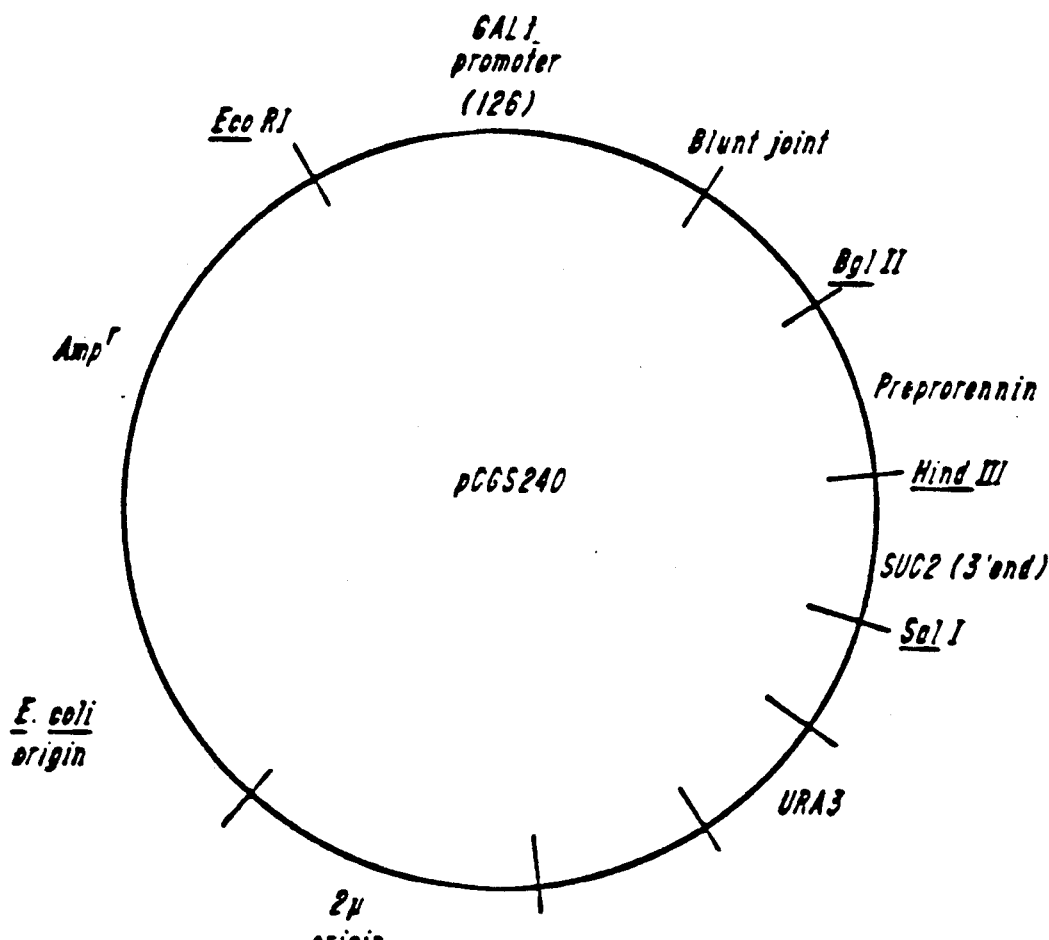
FIG. 7 is a diagrammatical showing of pCGS240.

A 1000 bp piece of DNA was obtained by digesting pCGS148 with EcoRI and BglII. In addition, the BglII/SalI 1800 bp fragment of pCGS168 was gel purified. These two fragments were ligated with the 8kb EcoRI/SalI fragment of pCGS 40 in excess. Transformation of competent *E. coli* CGE129 was carried out and restriction analysis revealed clones carrying the desired plasmid pCGS240 (FIG. 7). Plasmid DNA prepared from *E. coli* carrying pCGS240 was used to transform yeast strain CGY150. Yeast strain CGY457 resulted from that transformation and carries plasmid pCGS240. The level of expression of protein from the GAL1 promoter as demonstrated by western hybridization with rennin antibody was ~0.2% of the soluble protein.

Strain CGY457 bearing plasmid pCGS240 is on deposit with the American Type Culture Collection (ATCC), Accession Number 20661, deposited February, 1983.

While the specific embodiments of the invention have been shown and described, many variations are possible. For example, the present invention is mainly concerned with the use of a GAL1 promoter in the production of polypeptides such as bovine growth hormone, interferon, prorennin and pre-prorennin in yeast. Obviously, other protein products can be obtained and expressed using a GAL1 promoter of this invention in the operative relationship defined. Such polypeptides may be enzymes or other biologically active proteins. The foregoing examples are illustrative of the operation of such a mechanism.

What is claimed is:

1. A method of producing a heterologous polypeptide in yeast, said method comprising introducing the *Saccharomyces cerevisae* GAL1 promoter, which is repressed by glucose and induced by galactose operably linked to a heterologous gene other than one enclosing galactokinase in a chromosome or vector, in such a fashion that said chromosome or vector is replicated and carried by the cell as part of its generic information and expressing said gene under inducing conditions.

2. A method as in claim 1, wherein said gene is foreign to the yeast genome.

3. A method as in claim 1, wherein said polypeptide is a bovine growth hormone and said gene is a bovine growth hormone gene.

4. A method as in claim 1, wherein said polypeptide is interferon and said gene is an interferon gene.

5. A method as in claim 1, wherein said polypeptide is prorennin and said gene is a prorennin gene.

6. A method as in claim 1, wherein said polypeptide is pre-prorennin and said gene is a pre-prorennin gene.

7. A method as in claim 1, wherein said yeast is of the species *Saccharomyces cerevisiae*.

8. A DNA segment containing the *Saccharomyces cerevisiae* GAL 1 promoter which is repressed by glucose and induced by galactose operably linked to a heterologous gene and which promoter directs the expression of said heterologous gene within a yeast cell.

9. A DNA segment as in claim 8, wherein said gene is a bovine growth hormone gene.

10. A DNA segment as in claim 8, wherein said gene is an interferon gene.

11. A DNA segment as in claim 8, wherein said gene is a prorennin gene.

12. A DNA segment as in claim 8, wherein said gene is a pre-prorennin gene.

13. A DNA segment as in claim 8, wherein said GAL1 promoter has the sequences of bases 1-755 as shown in FIG. 8.

14. The recombinant DNA sequence

P$_{GAL1}$ - A A A A A A C C C C G G A T C T C G
A C C - A T G - X of *Saccharomyces cerevisiae* where P$_{GAL1}$ is the 1-820 base-pair DNA sequence for the GAL1 promoter for galactokinase, as shown in FIG. 8, and X is the DNA sequence for a polypeptide to be expressed in yeast.

15. The recombinant DNA sequence as in claim 14, wherein said polypeptide is bovine growth hormone.

16. The recombinant DNA sequence as in claim 14, wherein said polypeptide is interferon.

17. The recombinant DNA sequence as in claim 14, wherein said polypeptide is prorennin.

18. The recombinant DNA sequence

P$_{GAL1}$ - T T A T T C C T C T A C C G G A T C
A A - A T G - X of *Saccharomyces cerevisiae* where P$_{GAL1}$ is the 1-755 base-pair DNA sequence GAL125 for the GAL1 promoter for galactokinase, as shown in FIG. 8, and X is the DNA sequence for a polypeptide to be expressed in yeast.

19. The recombinant DNA sequence as in claim 18, wherein said polypeptide is pre-prorennin.

20. A replication chimeric plasmid having modifications comprising:

a fragment of the *Saccharomyces cerevisiae* 2 micron plasmid containing an initiation site for replication inserted at the PvuII site of YIp5, and a fragment from yeast chromosomal DNA containing the GAL1 promoter of *Saccharomyces cerevisiae* at the EcoRI site of said chimeric plasmid.

21. A plasmid as in claim 20, having a bovine growth hormone gene liked to the 3' end of said GAL1 promoter.

22. A plasmid as in claim 20, having an interferon gene linked to the 3' end of said GAL1 promoter.

23. A plasmid as in claim 20, having a prorennin gene linked to the 3' end of said GAL1 promoter.

24. A plasmid as in claim 20, having a pre-prorennin gene linked to the 3' end of said GAL1 promoter.

25. An integrating chimeric plasmid comprising a fragment from yeast chromosomal DNA containing the GAL1 promoter of *Saccharomyces cerevisiae* at the EcoRI site of YIp5.

26. A plasmid as in claim 25 having a bovine growth hormone gene linked to said GAL1 promoter.

27. A plasmid as in claim 25 having an interferon gene linked to said GAL1 promoter.

28. A plasmid as in claim 25 having a prorennin gene linked to said GAL1 promoter.

29. A plasmid as in claim 25 having a pre-prorennin gene linked to said GAL1 promoter.

30. The chimeric DNA material found in the yeast strain identified as American Type Culture Collection Accession Number 20643, Strain Designation CGY196, where said material comprises the GAL1 promoter linked to a bovine growth hormone gene.

31. The chimeric DNA material found in the yeast strain identified as American Type Culture Collection Accession Number 20661, Strain Designation CGY457, where said material comprises the GAL1 promoter linked to a pre-prorennin gene.

32. The chimeric DNA material found in the yeast strain identified as American Type Culture Collection Accession Number 20662, Strain Designation CGY461, where said material comprises the GAL1 promoter linked to a prorennin gene.

33. The chimeric DNA material found in the yeast strain identified as American Type Culture Collection Accession Number 20663, Strain Designation CGY528, where said material comprises the GAL1 promoter linked to an interferon gene.

* * * * *